United States Patent
Fukunaga et al.

(10) Patent No.: US 6,874,500 B2
(45) Date of Patent: Apr. 5, 2005

(54) BREATHING CIRCUITS HAVING UNCONVENTIONAL RESPIRATORY CONDUITS AND SYSTEMS AND METHODS FOR OPTIMIZING UTILIZATION OF FRESH GASES

(76) Inventors: Atsuo F. Fukunaga, P.O. Box 5101, Palos Verdes Peninsula, CA (US) 90274; Alex S. Fukunaga, P.O. Box 5101, Palos Verdes Peninsula, CA (US) 90274; Blanca M. Fukunaga, P.O. Box 5101, Palos Verdes Peninsula, CA (US) 90274

( * ) Notice: Subject to any disclaimer, the term of this patent is extended or adjusted under 35 U.S.C. 154(b) by 71 days.

(21) Appl. No.: 10/254,700

(22) Filed: Sep. 24, 2002

(65) Prior Publication Data

US 2003/0075176 A1 Apr. 24, 2003

Related U.S. Application Data

(60) Provisional application No. 60/340,206, filed on Dec. 12, 2001, and provisional application No. 60/324,554, filed on Sep. 24, 2001.

(51) Int. Cl.[7] .............................................. A61M 16/00
(52) U.S. Cl. ........................... 128/204.18; 128/203.12; 128/205.11; 128/911; 128/912
(58) Field of Search ...................... 128/207.14, 202.27, 128/911, 912, 204.18, 204.22, 205.11, 205.17, 203.12

(56) References Cited

U.S. PATENT DOCUMENTS

| | | | |
|---|---|---|---|
| 3,556,097 A | 1/1971 | Wallace |
| 3,713,440 A | 1/1973 | Nicholes |
| 3,856,051 A | 12/1974 | Bain |
| 4,007,737 A | 2/1977 | Paluch |

(Continued)

FOREIGN PATENT DOCUMENTS

| | | | |
|---|---|---|---|
| AT | 93941 | 8/1923 | |
| EP | 0 462 412 A2 | 12/1991 | |
| EP | 01 11 7999 | 12/2001 | |
| GB | 1 270 946 | 4/1972 | .......... A61M/16/00 |
| WO | WO 85/05277 | 12/1985 | |
| WO | WO 91/19527 | 12/1991 | |
| WO | PCT/US03/08292 | 12/2003 | |

OTHER PUBLICATIONS

Andrews, J. Jeffrey, *Inhaled Anesthetic Delivery Systems*, Anesthesia, Fourth Edition, pp. 185; and 203–207.

Byrick, R.J., et al., "Rebreathing and Co-Axial Circuits: A Comparison of the Bain and Mera F", *Canad. Anaesth. Soc. J.*, vol. 28, pp. 321–328 (1981).

(Continued)

*Primary Examiner*—Aaron J. Lewis
*Assistant Examiner*—Darwin P. Erezo
(74) *Attorney, Agent, or Firm*—Daniel B. Schein, Esq.

(57) ABSTRACT

A breathing circuit comprising first and second conduits, wherein at least one of the conduits is a non-conventional conduit. In an embodiment, a multilumen unilimb breathing circuit has first and second conduits, wherein when the proximal ends of said first and second conduits are each connected to an inlet and outlet fitting, respectively, movement of the distal end of the first conduit causes a corresponding movement of the distal end of the second conduit. In an embodiment, at least one of said conduits is coiled. In another embodiment, a coiled conduit is contained within an outer flexible conduit that is axially extendable and compressible, forming a unilimb multilumen respiratory circuit. The outer flexible conduit may be pleated to provide for non-rebounding axial extension and contraction. The multilumen respiratory circuit can provide a variable rebreathing volume. In an embodiment, at least one tube in a multilumen respiratory conduit is radially collapsible and radially expandable to a maximum radius for carrying respiratory gases to and from a patient. The methods and systems can be used to administer anesthesia and for other purposes.

9 Claims, 12 Drawing Sheets

U.S. PATENT DOCUMENTS

| | | | |
|---|---|---|---|
| 4,148,732 A | 4/1979 | Burrow et al. | |
| 4,188,946 A | 2/1980 | Watson et al. | |
| 4,232,667 A | 11/1980 | Chalon et al. | |
| 4,265,235 A | 5/1981 | Fukunaga | |
| 4,269,194 A | 5/1981 | Rayburn et al. | |
| 4,318,398 A | 3/1982 | Oetjen et al. | 128/201.13 |
| 4,336,798 A * | 6/1982 | Beran | 128/200.14 |
| 4,367,769 A | 1/1983 | Bain | 138/114 |
| 4,391,271 A | 7/1983 | Blanco | |
| 4,462,397 A | 7/1984 | Suzuki | |
| 4,463,755 A | 8/1984 | Suzuki | |
| 4,596,246 A | 6/1986 | Lyall | |
| 4,621,634 A | 11/1986 | Nowacki et al. | |
| 4,637,384 A | 1/1987 | Schroeder | |
| 4,657,532 A | 4/1987 | Osterholm | |
| 4,809,706 A | 3/1989 | Watson et al. | |
| 4,838,258 A * | 6/1989 | Dryden et al. | 128/204.18 |
| 4,938,210 A | 7/1990 | Shene | 128/203.12 |
| 4,967,744 A | 11/1990 | Chua | 128/204.18 |
| 5,088,486 A | 2/1992 | Jinotti | |
| 5,121,746 A | 6/1992 | Sikora | 128/203.12 |
| 5,140,983 A | 8/1992 | Jinotti | |
| 5,195,527 A | 3/1993 | Hicks | |
| 5,230,727 A | 7/1993 | Pound et al. | |
| 5,284,160 A | 2/1994 | Dryden | |
| 5,320,093 A | 6/1994 | Raemer | |
| 5,377,670 A | 1/1995 | Smith | 128/204.17 |
| 5,398,675 A | 3/1995 | Henkin et al. | 128/203 |
| 5,404,873 A | 4/1995 | Leagre et al. | |
| 5,546,930 A | 8/1996 | Wikefeldt | |
| 5,623,922 A | 4/1997 | Smith | 128/204.18 |
| 5,715,815 A | 2/1998 | Lorenzen et al. | |
| 5,722,391 A | 3/1998 | Rosenkoetter et al. | |
| 5,778,872 A | 7/1998 | Fukunaga et al. | 128/202.27 |
| 5,823,184 A * | 10/1998 | Gross | 128/204.18 |
| 5,901,705 A | 5/1999 | Leagre | |
| 5,983,891 A | 11/1999 | Fukunaga | 128/200.24 |
| 5,983,894 A | 11/1999 | Fukunaga et al. | 128/205.29 |
| 5,983,896 A | 11/1999 | Fukunaga et al. | 128/207.14 |
| 6,003,511 A | 12/1999 | Fukunaga et al. | 128/202.27 |
| 6,079,410 A * | 6/2000 | Winefordner et al. | 128/201.11 |
| 6,129,082 A * | 10/2000 | Leagre | 128/205.29 |

OTHER PUBLICATIONS

Dorsch, Jerry A., M.D., Dorsch, Susan E., M.D., *Understanding Anesthesia Equipment*, Chapter 7, The Circle Absorption System, pp. 201–202 and 220–221.

Forrest, P.R., "Defective Anaesthetic Breathing Circuit", *Canad. J. Anaesth.*, vol. 34, pp. 541–542 (1987).

Goresky, G.V., "Bain Circuit Delivery Tube Obstructions", *Canad. J. Anaesth.*, vol. 37, p. 385 (1990).

Hannallah, R., et al., "A Hazard Connected With Re–Use of the Bain's Circuit: A Case Report", *Canad. Anaesth. Soc. J.*, vol. 21, pp. 511–513 (1974).

Heath, P.J., et al., "Modified Occlusion Tests for the Bain Breathing System", *Anaesthesia*, vol. 46, pp. 213–216 (1991).

Jeretin, S. et al., "A Variable Deadspace Device for Use with the Engström Respirator", *Anesthesiology*, vol. 34, pp. 576–577 (1971).

Okazaki, et al., "Effect of Carbon Dioxide (Hypocapnia and Hypercapnia) on Regional Myocardial Tissue Oxygen Tension in the Dog", *Anesthesiology*, vol. 71, No. 3A, A486 (1989).

Okazaki, et al., "Effect of Carbon Dioxide (Hypocapnia and Hypercapnia) on Regional Myocardial Tissue Oxygen Tension in Dogs with Coronary Stenosis", *Anesthesiology*, vol. 73, No. 3A, A549 (1990).

Okazaki, et al., "Effect of Carbon Dioxide (Hypocapnia and Hypercapnia) on Internal Mammary–Coronary Arterial Bypass Graft Blood Flow and Regional Myocardial Oxygen Tension in the Dog", *Anesthesiology*, vol. 81, No. 3A, A717 (1994).

Paterson, J.G., et al., "A Hazard Associated with Improper Connection of the Bain Breathing Circuit", *Canad. Anaesth. Soc. J.*, vol. 22, pp. 373–377 (1975).

Pilbeam, Susan P., *Mechanical Ventilation, 2nd Ed., Mosby Year Book*, St. Louis, Missouri, pp. 285–286 (1992).

Pontoppidan, H., et al., "Acute Respiratory Failure in the Adult", *The New England Journal of Medicine*, vol. 287, pp. 743–752 (1972).

Robinson, S., et al., "Safety Check for the CPRAM Circuit", *Anesthesiology*, vol. 59, pp. 488–489 (1983).

Scott, P.V., et al., "Variable Apparatus Deadspace", *Anaesthesia*, vol. 46, No. 9, pp. 1047–1049 (1991).

Shapiro, B.A., et al., "Clinical Application of Respiratory Care", *Yearbook Medical Publishers, Inc.*, pp. 351–352 ("Principles of Ventilator Maintenance") (1979).

Stoyka, W., "The Reliability and Usefulness of the Suwa Nomogram in Patients in Respiratory Failure", *The Canadian Anaesthetists' Society Journal*, pp. 119–128 (1970).

Suwa, K., et al., "Change in $Pa_{CO_2}$ with mechanical dead space during artificial ventilation", *Journal of Applied Physiology*, vol. 24, pp. 556–561 (1968).

Advertisement of the CPRAM™ Coaxial Circuits by Dryden Corporation, Indianapolis, Indiana.

Advertisement of the ACE Breathing Circuit™ by Meridian Medical Systems, Inc., Indianapolis, Indiana.

Fletcher, R., Scott, P. V., Jones, R.P., "The variable deadspace is not necessary," Correspondence reported in *Anaesthesia*, vol. 47, No. 7, pp. 623–624 (1992).

Coetzee, J.F. et al., "Fresh gas flow is not the only derminant of volatile agent consumption . . . ," British Journal of Anaesthesia, 88 (1) pp 46–55 (2002).

Baum, J.A. et al., "Low–flow anaesthesia," Anaesthesia, vol. 50 (Supplement), pp 37–44 (1995).

Johansson, A. et al., "The Ouotient End–tidal/Inspired Concentration of Sevoflurane in a Low–Flow System," Journal of Clinical Anesthesia, 14, pp 267–270 (2002).

* cited by examiner

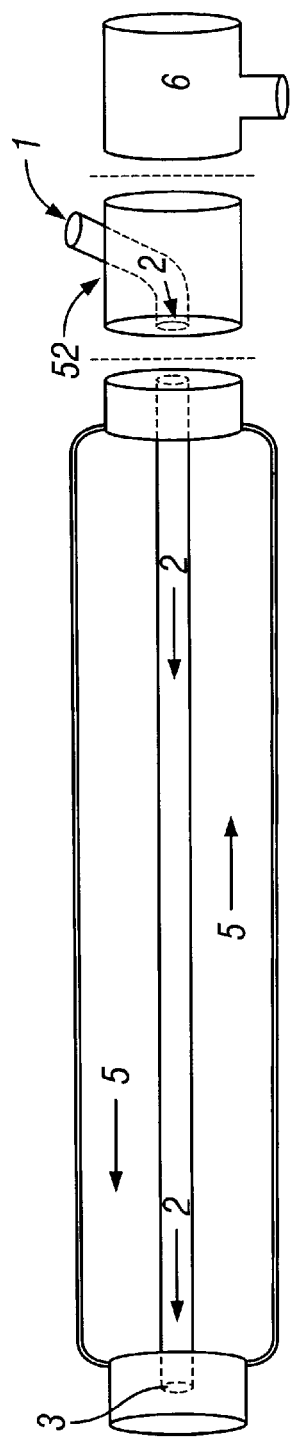
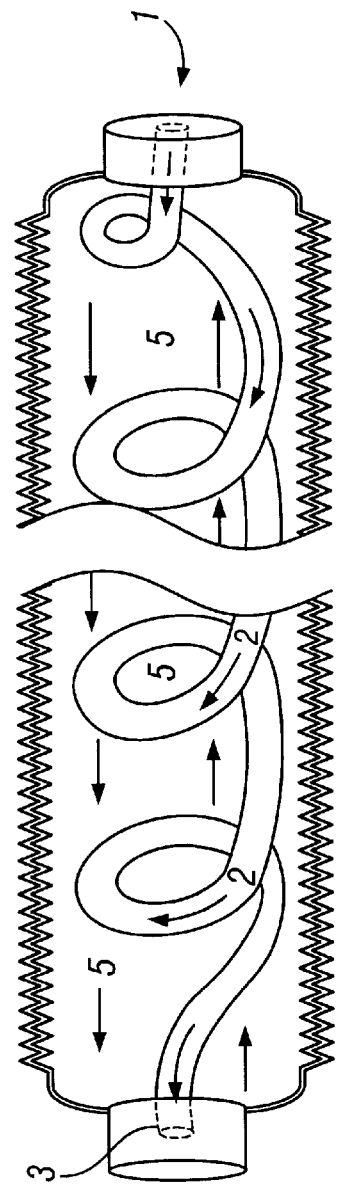
FIG. 4B
FIG. 4C

BREATHING CIRCUITS HAVING UNCONVENTIONAL RESPIRATORY CONDUITS AND SYSTEMS AND METHODS FOR OPTIMIZING UTILIZATION OF FRESH GASES

PRIORITY

This application claims priority of U.S. provisional patent application Ser. No. 60/340,206, filed Dec. 12, 2001 and U.S. provisional patent application Ser. No. 60/324,554, filed Sep. 24, 2001.

FIELD OF THE INVENTION

This invention relates to devices for use in resuscitating and/or providing anesthesia and/or assisted and artificial ventilation to patients, and more particularly relates to breathing circuits with interacting mutually adjustable length fluid carrying members, to a multilumen breathing circuit utilizing unconventional (or new era) conduits, and to systems and methods for optimizing utilization of fresh gases (e.g. anesthetic agents and oxygen) during provision of anesthesia and/or assisted and artificial ventilation.

BACKGROUND OF THE INVENTION

Assisted and/or artificial ventilation systems are an essential component of modern medicine. Generally, such systems provide inspiratory fresh gases to a patient from a source of same, such as from an anesthesia or a ventilator machine, and conduct expired gases away from the patient. Inspiratory gases are conducted through a different conduit from the expired gases and thus at least two conduits are required. Commonly used circuits have two limbs (e.g., two independent tubes). The ends of the tubes in a breathing circuit are generally held in spaced relationship by a connector located at the patient, or distal, end of the circuit. The connector can place the distal (i.e., patient) ends of the tubes in a fixed parallel relationship, or the connector can be a Y-piece with the two tubes converging at an angle. Conventional respiratory tubes are corrugated and flexible to permit movement while minimizing collapse and kinking of the tubes. Recently, the use of axially expandable and contractible pleated ("accordion-like") tubing has become popular. Commonly used accordion-like or pleated tubing is known as ULTRA-FLEX® (available from King Systems Corporation, Noblesville, Ind., U.S.A.), FLEXITUBE® or ISOFLEX™, in which the length can be adjusted by axially expanding or contracting one or more pleats between a closed and open position. Whether the pleats are in the open or closed position, the tube wall remains corrugated to minimize the risk of kinking or collapse upon convolution or bending of the tubing.

Respiratory Care and ICU Type Non-Rebreathing System

In a non-rebreathing breathing system, which can be used for respiratory care or in an intensive care unit (ICU), a one-way valve permits gases to flow to a patient through an inspiratory conduit, while another one-way valve causes expired gas from the patient to flow through an expiratory conduit and then to an exhaust conduit.

Circle $CO_2$ Absorption and Mapleson Type Breathing Systems

In a "circle system," a one-way valve permits gas to flow to a patient through a first or inspiratory conduit, while another one-way valve permits partial recirculation of the gases by causing expired gases to flow from the patient through a second or expiratory conduit to a "recirculation module" or "scrubber circuit", which generally comprises a carbon dioxide absorber to eliminate the expired carbon dioxide resulting in "scrubbed gases". The scrubbed gases are then combined with the fresh gases coming from the anesthesia machine, and the mixed gases are referred to herein as "refreshed gases". Some or all of the refreshed gases can be rebreathed by the patient. Excess gases are directed to an exhaust conduit and/or scavenger. Thus, new fresh gases are combined with scrubbed gases at the scrubber circuit, and are delivered as refreshed gases to the first conduit, while expired gases are carried by a second conduit to a "scrubber circuit" for re-circulation and/or exhaust.

It is believed that in low flow anesthesia with the circle system, the anesthetic concentration of the refreshed gases decreases progressively from the initial fresh gas concentration (concentration at the vaporizer) in the process of re-circulation. Such a decrease may be due to dilution by the expired gases and/or scrubbed gases, leakage, and adsorption and/or absorption by plastic, rubber and other materials in the system. Therefore, low flow anesthesia, including totally closed anesthesia using prior art circle systems, is in theory possible, but very limited in practice.

In Mapleson A-F type circuits, fresh gas is delivered into a common breathing tube by a fresh gas delivery/supply tube, wherein the breathing tube acts to provide gases to the patient and receive expired gases therefrom. Generally, the diameter of the fresh gas supply tube is small thereby limiting its function to being a fresh gas delivery or supply conduit rather than an inspiratory tube (i.e., a tube from which a patient directly inspires as in a circle system). A Mapleson D type circuit (the most commonly used circuit among the Mapleson circuits) does not use valves, therefore, the flow of fresh gases required is sufficiently high to minimize $CO_2$ rebreathing. During inspiration, the patient will inhale fresh gases from the fresh gas delivery/supply tube inlet and gases from the common breathing tube, which may be a mixture of fresh gas and expired alveolar gases. High fresh gas flow will flush the breathing tube, pushing the expired alveolar gases out of the circuit.

The Bain Circuit

An embodiment of a unilimb modification of the Mapleson D type circuit, often referred to as a "Bain circuit" or "Bain," is described in U.S. Pat. No. 3,856,051, in which the fresh gas delivery line is inserted through the wall of the common breathing tube near the proximal rather than near the distal end thereof, and the delivery tube then extends lengthwise through the common breathing tube so that its distal end is near the distal end of the common breathing tube. This creates a unilimb circuit from dual members. The fresh gas delivery line is sealably bonded to the common breathing tube at its junction therewith.

Another embodiment of a Mapleson D type circuit is described in U.S. Pat. No. 5,121,746, to Sikora, in which a flexible corrugated tube is divided by an internal common wall into a larger and smaller flow passage and is provided with a bayonet type connector at the patient end and a double friction fit connector at the machine end. A modification of the circuit described in this patent is used to form a circle circuit sold as the Limbθ™ by Vital Signs, Inc. of Totowa, N.J., USA.

The Universal F® Circuit

With reference to U.S. Pat. No. 4,265,235, to Fukunaga, a unilimb device of universal application for use in different types of breathing systems is described which provides many advantages over prior systems. The Fukunaga device, sold as the Universal F® by King Systems Corporation of Noblesville, Ind., U.S.A., utilizes a space saving co-axial, or tube within a tube, design to provide inspiratory gases and remove expiratory gases. Numerous advantages flow from this arrangement, such as a reduction in the size of the breathing apparatus connected to a patient. Further, the device acts as an artificial nose since the expired gases warm and maintain humidity of the inspired gases as the two opposing flows are countercurrent in the unilimb device.

Universal F2® Technology

With reference to U.S. Pat. No. 5,778,872, to Fukunaga et al., unilimb multi-lumen circuits are disclosed and embodiments thereof are sold as the F2™ or Universal F2® by King Systems Corporation of Noblesville, Ind., U.S.A., which have revolutionized artificial ventilation systems and methods of providing assisted ventilation and anesthesia. The F2™ system provides for safe and ready attachment and detachment of multilumen (e.g., co-axial) system components from the proximal terminal. This permits more efficient placement and utilization of other breathing circuit components, improves system performance, and yet reduces medical waste and costs. In general, the Universal F® and the F2™ are used in a circle system configuration with a carbon dioxide absorber. For more information about the F2™ technology, one may contact King Systems Corporation.

For further information on breathing systems, and anesthetic and assisted ventilation techniques, see U.S. Pat. Nos. 3,556,097, 4,007,737, 4,188,946, 4,265,235, 4,463,755, 4,232,667, 5,284,160, 5,778,872, Austrian Patent No. 93,941, British Patent 1,270,946, Dorsch, J. A., and Dorsch, S. E., *Understanding Anesthesia Equipment: Construction, Care And Complications* Williams & Wilkins Co., Baltimore (1974), and Andrews, J. J., "Inhaled Anesthetic Delivery Systems," in *Anesthesia*, 4$^{th}$ Ed. Miller, Ronald, M. D., Editor, Churchill Livingstone, Inc., N.Y. (1986). The text of all documents referenced herein, including documents referenced within referenced documents, is hereby incorporated by reference as if same were reproduced in full below.

Cost Effective Anesthesia Systems and Unconventional New Era Respiratory Conduits Hospitals, medical personnel, and related entities are always looking for ways to improve medical care. Numerous monitoring standards have been implemented to ensure that the required medical care is being safely administered. For example, in the field of respiratory care and anesthesia, non-invasive and invasive monitoring methods have become routinely used, such as alarm monitoring systems that warn the user of obstruction and/or disconnection of gas flows, inspired and end-tidal gas monitoring, oxygen saturation monitoring by pulse oximeter, arterial blood gas and mixed venous blood gas monitoring. These techniques and devices enable continuous patient monitoring, which permits the vigilant healthcare practitioner to more accurately adjust or titrate the necessary dosages of anesthetic gases or drugs, and readily detect problems due to the pathophysiologic condition of the patient or due to those caused by medical equipment failure or settings. There is a desire for an anesthesia system that can optimize the use of such expensive monitoring equipment, which for example, could be used to decrease the waste of anesthetic gases.

Respiratory care is commonly and increasingly provided in medicine. Respiratory care includes, for example, artificial ventilation techniques, such as assisted ventilation and/or oxygen therapy. Certain devices widely used in respiratory care include breathing circuits, filters, HME's (heat and moisture exchangers), endotracheal tubes, laryngeal masks, laryngeal tubes, and breathing masks. Breathing circuits comprised of rigid pipes or flexible corrugated tubes made of rubber, plastic or silicon flexible tubes have been widely used all over the world for almost a century. In order to prevent cross contamination, "single use" breathing circuits are disposed of after a single use, or alternatively, more sturdy and more expensive reusable breathing circuit are used that can be sterilized by autoclave or other means. Both types of circuits are expensive to produce and/or use. Sterilization of the circuit requires substantial labor and processing costs, likewise disposing of the breathing circuit after a single use, while it is very effective in preventing cross contamination, also results in additional cost to the hospital.

U.S. Pat. No. 5,901,705, to Leagre, discloses a sleeve and filter for a breathing circuit, wherein the filter and a tubular sleeve or sheath encase a breathing circuit during use. The filter housing has two ports, one port is for connection to a patient and the other to the distal end of a breathing circuit. The sleeve is connected to the exterior of the filter housing and is extendable in a proximal direction over the breathing circuit. After use, the filter and sleeve are discarded, while the breathing circuit is reused for multiple patients. The sleeve and filter reduces the need for sterilizing the circuit after each use. The sleeve is constructed of a lightweight, relatively inexpensive material to help minimize the costs of producing the sleeve member. A clear, extruded polyethylene, polypropylene or polyvinyl film having a thickness generally similar to a heavy-duty plastic food storage bag has been found to perform admirably in this role as a sleeve member. The sleeve does not serve as a conduit for providing or exhausting respiratory gases.

U.S. Pat. No. 5,377,670, to Smith, discloses a casing or envelope for a breathing circuit to reduce heat transfer between the corrugated tube and the ambient atmosphere, thus the case or sleeve of the breathing circuit serves as an insulation means. The envelope or casing is not a conduit for providing inhaled and receiving exhaled gases. U.S. Pat. No. 5,983,896, to Fukunaga, discloses a multilumen unilimb breathing circuit that provides the advantages of maintaining humidity and temperature due to the counter-current effect of the gases.

While the above devices fulfill their respective, particular objectives and requirements, the aforementioned patents and the prior art do not describe a device wherein at least one of the respiratory conduits is comprised of a non-conventional (also referred to as "new era") pipe or tube (i.e., different from a rigid-walled tube, pipe, corrugated tube, or pleated tube), which is both axially and radially flexible, but which has little or no compliance beyond a certain conduit radius and/or volume. By radially flexible, it is meant that the diameter of the conduit can be substantially reduced or the conduit can be relaxed or collapsed in cross-section in comparison to rigid-walled conventional tubing. This is distinguished from axially bending the tubing without substantially altering the cross-sectional area of the tube at the bend as is possible with rigid-walled prior art tubing. Prior art rigid-walled respiratory conduits maintain patency under ambient conditions as well as under the pressure differentials between their interior and exterior that occur during use for providing inspiratory and/or receiving expiratory gases. Since these prior art respiratory conduits do not radially collapse under ambient conditions (e.g., when not in use), they require greater space for shipping and storage, and they require thicker walls to have sufficient rigidity to avoid collapse under ambient and operating conditions. Thus, a greater amount of plastic is used to produce such tubing, which increases costs, as well as the volume of the waste produced.

In general, circuit compliance (i.e., expansion of the volume of circuit tubing under operating pressures) is undesired as it interferes with the accuracy and precision of gas administration. Further, excessive compliance may lead to insufficient gases reaching the patient's lungs.

The present inventors discovered that, so long as the respiratory conduits, and preferably the inspiratory conduit, can maintain patency for inspiratory and expiratory gases, the conduits do not need to be always patent like rigid-walled pipes or tubes (e.g., corrugated plastic tubes that maintain a fixed diameter at ambient conditions and/or which are relatively rigid or straight). The respiratory conduits of the present invention should, however, provide low resistance and little compliance during use sufficient to meet the requirements for spontaneous and assisted ventilation. It is preferred that the inspiratory conduit permit gas flow at all times, and even under negative pressure, and that the expiratory line provide positive pressure even in spontaneous ventilation.

Definitions

To facilitate further description of the prior art and the present invention, some terms are defined immediately below, as well as elsewhere in the specification. As used herein, the term "artificial or assisted ventilation" shall also incorporate "controlled and spontaneous ventilation" in both acute and chronic environments, including during anesthesia. Fresh gases include gases such as oxygen and anesthetic agents such as nitrous oxide, halothane, enflurane, isoflurane, desflurane, sevoflurane, that are generally provided by a flowmeter and vaporizer. The end of a conduit directed toward a patient shall be referred to as the distal end, and the end of a conduit facing or connected to a source of inspiratory gases shall be referred to as the proximal end. Likewise, fittings and terminals or other devices at the distal end of the breathing circuit, e.g., connecting to or directed at the patient airway device (i.e., endotracheal tube, laryngeal mask, laryngeal tube, face mask etc.), will be referred to as distal fittings and terminals, and fittings and terminals or other devices at the proximal end of the breathing circuit will be referred to as proximal fittings and terminals. So, a distal adaptor or connector would be located at the distal or patient end of a circuit.

It is generally understood that a proximal terminal in a multilumen unilimb breathing circuit context is located at the machine end of the circuit and separates at least two independent flow paths that are in parallel closely-spaced or apposed relationship or that are coaxial in the circuit so that at least one flow path can be connected to a source of inspiratory gases while another flow path can be connected to an exhaust port that is spaced from the inspiratory gas port. A proximal terminal may also comprise a rigid housing that merges two independent flow paths into a common flow path, for example a Y-type fitting, preferably with a septum. The use of a proximal fitting with a proximal terminal in a unilimb circuit is a new concept brought about by the Universal F2® inventions, which for the first time made it possible to readily connect and disconnect plural tubes to a proximal terminal on an assisted ventilation machine via a corresponding proximal fitting. Unlike the proximal terminal, when a proximal fitting comprises multiple lumens, the proximal fitting maintains the spatial relationship of the proximal ends of the tubes forming a multilumen circuit. Hence a proximal fitting in a breathing circuit is to generally be understood as a fitting which permits ready connection of tubing to a proximal terminal which can provide inspiratory gases and exhaust expiratory gases from separate spaced ports. In some embodiments of the present invention tubing may be directly bonded to a proximal terminal, while in other embodiments tubing may connect to a proximal fitting that can engage a corresponding port or ports on a proximal terminal. The proximal fitting may include filter means, or may engage a filter which in turn connects to a proximal terminal.

The term conduit broadly comprises fluid carrying members without being limited to conventionally used corrugated tubes, such as those used in presently available breathing and/or anesthesia circuits (i.e., a conduit has a lumen defined by one or more walls, has a variety of shapes and diameters, and serves the purpose of carrying inspiratory gases to or expiratory gases from a patient). For example, conduits for use with the present inventions may comprise flexible fabric or plastic sheaths (like a film or sheet made of plastic, such as polyvinyl, that can have a cylindrical or tubular form when gases or fluid are contained, but collapses or looses the tubular form when deflated or emptied) and/or flexible tubes that may be smooth-walled, straight, corrugated, collapsible, and/or coiled. In this respect, certain embodiments of the present invention substantially depart from the conventional concept and design of prior art respiratory conduits. Embodiments of flexible conduits for carrying respiratory gases to and/or from a patient in accordance with the present invention can be both flexible in the radial and axial directions up to a maximum volume and/or radius (or maximum cross-sectional area where the cross-sectional shape is not circular), and have a wide variety of cross-sectional shapes, and in so doing provide a low cost apparatus very well suited to providing respiratory care, i.e., assisted ventilation to a patient, which is effective and practical.

Unconventional or non-conventional tubular conduits refer to conduits used in a respiratory circuit for carrying patient inspiratory and/or expiratory gases that are made of materials and/or have shapes not previously used in assisted ventilation or anesthesia machines for carrying inspiratory and expiratory gases between a patient or other mammal and the machine. By carrying patient inspiratory and/or expiratory gases, it is understood that the gases are being provided via a conduit to a patient from a source (e.g., ventilator machine) and exhausted via the same and/or another conduit to an exhaust (e.g., assisted ventilation machine). For example, a coiled inspiratory or expiratory conduit when used in accordance with the present invention is a non-conventional tubular conduit. Likewise, a conduit formed of flexible, gas impermeable fabric, such as but not limited to extruded polyethylene, polypropylene or polyvinyl film, that is radially expandable to a maximum radius and volume under pressures generally used in assisted respiration and is collapsible when the pressure inside of same is less than ambient pressure or the pressures generally used in assisted respiration, can be used as a non-conventional respiratory conduit in accordance with the present invention. Ambient pressure refers to the pressure normally encountered outside of tubes, which is generally atmospheric pressure. Such conduits can maintain patency as needed in use yet readily relax or collapse (collapsing may require some assistance depending on the embodiment) to smaller diameters, lengths, and volumes, particularly when the internal pressure inside is sufficiently lower than the pressure outside of the conduit.

For the purposes of brevity, the term Suave™ flexible tube is used to describe a flexible respiratory conduit for use in carrying respiratory gases (i.e., gases to be inspired and expired gases to be exhausted) between a patient and a ventilation machine or respiratory care device in which the conduit is radially collapsible when not in use, and can expand to a maximum predetermined diameter (or maximum cross-sectional area; maximum diameter and maximum radius incorporate maximum cross-sectional area when the cross-sectional shape is not circular) and volume during use (such a conduit shall be hereinafter referred to in this document as a suave tube or suave conduit; no trademark rights are waived by use of the term suave or any other mark used herein regardless of case or inclusion of the ™ or ® symbol). Upon expansion to its maximum diameter (i.e., maximum cross-sectional area) a suave tube exhibits substantially the same compliance in assisted ventilation applications as conventional corrugated tubes or pleated tubing (i.e., ULTRA-FLEX®) conduits. Suave flexible tubes may also be axially expanded or contracted. Suave tubes are much less expensive to manufacture than conventional conduits having a relatively rigid diameter or cross-sectional shape, such as those formed of corrugated tubing.

Preferred radially collapsible tubes for use in the present invention will, when inflated at pressures encountered in providing assisted ventilation and/or anesthesia to humans and other mammals, have a compliance of less than about 50%, preferably less than about 20%, more preferably less than about 10%, even more preferably less than about 5%, and most preferably less than about 2%. Preferred radially collapsible tubes for use in the present invention have a minimum cross-sectional area when fully inflated sufficient to meet the desired flow characteristics (hereinafter, referred to as the inflated cross-sectional area), and can collapse so that the collapsed cross-sectional area is preferably less than about 90% of the inflated cross-sectional area, more preferably less than about 70% of the inflated cross-sectional area, even more preferably less than about 50% of the inflated cross-sectional area, even more preferably less than about 25% of the inflated cross-sectional area, and most preferably less than 10% of the inflated cross-sectional area.

In one embodiment, the suave tubes are shipped and stored in collapsed form, and after inflation thereof no subsequent effort may be made to collapse them, except optionally to compress the suave tubes to a smaller volume for disposal. In this way, manufacture, shipping and storage costs are minimized. Gravitational forces will cause the suave tubes to collapse to varying degrees in some embodiments when not pressurized sufficiently.

Breathing Circuit Requirements

A patient requiring artificial ventilation or anesthesia may be positioned in an awkward position and depending on the surgical site the required length of the circuit may vary. This is also so in patients undergoing diagnosis, e.g., MRI, CT scans, etc. It is therefore desirable to have a breathing circuit that is flexible and that the length of both the inspiratory or fresh gas delivery tube and the expiratory or exhaust tube can be adjusted while minimizing disconnections, obstructions, entangling and kinking. It is also desirable to have breathing circuits that are light in weight. Furthermore, for cost containment, the health care providers (i.e., hospital, physician, ambulatory surgery center, nursing homes, etc.) require inexpensive breathing circuits and/or inexpensive methods to provide artificial ventilation or anesthesia to patients in need thereof.

Breathing circuits may be classified based on how carbon dioxide is eliminated. Carbon dioxide can be eliminated by "washout", which is dependent on the fresh gas inflow (i.e., $CO_2$ absorption is not required, e.g., in a Mapleson type circuit), or by using a $CO_2$ absorber such as soda lime and the like, (i.e., as in a circle circuit). Thus, breathing circuits in anesthesia are generally provided as circle circuits ($CO_2$ absorption system) or Mapleson type circuits. Because Mapleson D type partial rebreathing systems require high fresh gas flows, the circle system is the most widely accepted system. Breathing systems wherein low fresh gas flow can be utilized are advantageous because of reduced consumption and waste of fresh gases (e.g., anesthetic gases), ecological benefits (reduced environmental pollution), and cost-savings. However, a major concern of low flow techniques in anesthesia is the efficiency of fresh gas utilization and the unpredictability concerning the alveolar or inspired concentration of anesthetics provided to the patient that should be administered in sufficient dosages to achieve desired anesthetic endpoints (e.g., avoid awareness during surgery without overdosing). Moreover, there is a significant discrepancy between the volatile anesthetic vaporizer setting concentration and the inspired concentration of anesthetic gases. A further concern with the circle system is the interaction of volatile anesthetics with the carbon dioxide absorber (e.g., soda lime), which has been recently reported as producing toxic substances. This concern includes the formation of carbon monoxide and Compound A during degradation of volatile anesthetics by soda lime. For example, CO has been found in anesthetics, including halothane, enflurane, isoflurane and desflurane circle systems. Moreover, in the case of sevoflurane, it is known that sevoflurane is degraded in the presence of soda lime to olefin and Compound A, which has been reported to have nephrotoxic potential at clinical concentrations. Further, it is desired to reduce waste of expensive anesthetic and respiratory gases in circle systems and Mapleson type systems.

A major concern with prior unilimb breathing circuits is that the inspiratory gas or fresh gas line not become disconnected or blocked (e.g., via kinking) during use. For this reason, rigidly bonding the proximal end of the inspiratory gas line to the fresh gas inlet fitting was stressed, while the distal end was permitted to move with respect to the distal end of the outer conduit (e.g., exhaust conduit), which could create a variable dead space. Despite the surprising discovery reported in U.S. Pat. No. 5,778,872, to Fukunaga, that an appropriate dead space in a breathing circuit could be beneficial by yielding normocapnia without hypoxia, there is still a desire for a circuit that has either a minimum and/or fixed dead space regardless of circuit manipulation, yet is flexible and safe. Further, there is a desire for systems that more efficiently utilize anesthetic gases in a safe and predictable manner. It is also desired that the same breathing circuit be utilized in both adult and pediatric cases, or at least in a greater number of patients, thereby minimizing the need for circuits of different size. There is also a need for breathing circuits and systems that are simpler, lightweight, cost-effective, safer, and/or easier to operate and handle than prior circuits and systems.

SUMMARY OF THE INVENTION

An embodiment of the present invention includes a breathing circuit, wherein at least one of the respiratory conduits is a non-conventional conduit. Thus, in a unilimb, dual limb or a multilimb circuit, a non-conventional conduit may be used to carry inspiratory and/or expiratory gases between a patient or other mammal and a machine. For example, in an embodiment, at least one tube in the circuit may be a collapsible or suave tube, or may be a spiral or coiled tube. Such circuits may be referred to as F3™ circuits or Universal F3™ circuits (no waiver of trademark rights is made hereby for these or other marks used herein).

An embodiment of the present invention includes a multilumen respiratory circuit comprising first and second conduits, wherein the proximal ends of the first and second conduits can each be connected to a respective inlet or outlet fitting, and movement of the distal end of the first conduit causes a corresponding movement of the distal end of the second conduit. Thus, the circuit members interact so that axial extension or contraction of one member causes a corresponding axial extension or contraction in length of a second member. This latter type of circuit may also be referred to herein as an F3™ contractible circuit or a Universal F3™ circuit. In an embodiment, at least one of the conduits is a coiled tube. In another embodiment, a coiled tube is contained within an outer flexible tube that is axially extendable and compressible, forming a unilimb multilumen respiratory circuit, which may also be referred to herein as an F Coil™ circuit.

In an embodiment, the outer flexible conduit may be a pleated tube or a non-conventional conduit to provide for axial extension and contraction. In an embodiment, an accordion-like tube (e.g., UTLRA-FLEX® tube), is divided internally by a common wall that is made of a flexible plastic or gas-impermeable fabric that allows simultaneous radial expansion of one lumen while causing contraction of the other lumen(s) sharing the common flexible wall. In another embodiment, a non-conventional conduit can be joined side by side with a pleated tube either by continuous or spaced attachment. Further, two or more Suave™ tubes can be used together to create a multi-lumen Suave™ tube respiratory conduit. Such a multi-lumen Suave™ tube respiratory conduit can be manufactured by extruding a tube of flexible plastic in much the same way plastic storage bags are formed. However, rather than heat sealing radially across the extruded tube to form a bag, axial seams can be heat formed in the axial direction to form separate gas carrying lumens.

Proximal and distal fittings can be bonded at the proximal and/or distal ends of the lumens in the respiratory conduit devices of the present invention to facilitate operative connection to machines and patients, respectively.

An embodiment of the present invention includes a multilumen respiratory conduit comprising at least first and second flexible tubes, wherein the proximal ends of the first and second flexible tubes can each be connected to an inlet or outlet fitting, and wherein at least one of the flexible tubes is comprised of a non-conventional plastic tubular material (e.g., formed of a flexible fabric, such as polyvinyl). Such a respiratory conduit is capable of maintaining respiratory patency under the range of conditions encountered in providing respiration, whether spontaneous or assisted ventilation (i.e., affording free passage of inspiratory and expiratory gases), but may partially or substantially completely collapse when not in use. Such a tube can be shipped in collapsed or substantially collapsed form. The tubes forming the multilumen respiratory conduit can be arranged side by side, have periodic connections to one another, or one can be contained within another, and their shapes can be greatly varied. For example, a circular cross-sectional shape is not necessary. The distal and proximal ends of each tube can be formed of a more rigid material than the rest of the tube or be bonded to a fitting to facilitate connection to an inspiratory gas source, an exhaust outlet, to a carbon dioxide canister for recirculation of gases such as that used in an anesthesia machine, and to airway devices such as respiratory masks and endotracheal tubes.

The present invention also involves new systems and methods of optimizing utilization of fresh gases during artificial or assisted ventilation, including administering anesthesia. In an embodiment, a Mapleson D type system is modified and combined with a modified $CO_2$ absorption circle system to produce an efficient system, wherein the system is capable of optimizing the utilization of anesthetic gases in a safe and predictable manner. By providing undiluted fresh gases at the patient side (i.e., distal end of the circuit) and circulating the expired gases through a scrubber circuit having a carbon dioxide absorber, the system provides assurance that the patient receives more accurate fresh gas concentrations (i.e., close to the anesthesia machine flow meter's oxygen concentration and the volatile anesthetic vaporizer's concentration setting). In addition, recirculating the gases allows re-use of the gases after $CO_2$ elimination, thereby providing reliable low flow anesthesia. As a result, utilization of fresh gases is optimized. Furthermore, by using a unilimb multilumen breathing circuit wherein the dimensions of at least one of the breathing conduits can be altered to adjust the volume therein or by using mutually adjustable length members, the anesthetic concentration and amount of rebreathing can be safely adjusted and predictably optimized, and the same breathing conduit or circuit may be utilized universally in adult and pediatric cases.

The circuits do not need to be individually packaged, but more than one circuit can be packaged together. An advantage of having several circuits packed together is that the packaging can be more compact, also reducing storage and shipping costs, and waste. Furthermore, only one bag or box needs to be opened instead of several plastic bags, which decreases set up time. All of the above savings can be substantial as they help optimize operating room utilization (e.g., reduced waiting time for professionals between operations due to reduced operating room cleaning and set up time). Therefore, the present invention enhances health care cost-effectiveness beyond device cost savings. The circuits and systems of the present invention are simple, compact and lightweight to facilitate storage and shipping, use less plastic and result in less medical waste being generated, and are safe, practical, easy to handle, protect the environment and promote cost-effective artificial ventilation.

The present invention may be better understood by reference to the figures and further detailed description below. For the purposes of facilitating understanding of the invention, in the following figures certain fitting components are not shown and/or certain fitting components are shown in simplified form. For example, struts or flanges for spacing components from one another are not be shown, and wall thickness and relative tube diameters and lengths are not to scale.

DESCRIPTION OF THE FIGURES

FIGS. 4A–C illustrate the components and operation of a system constructed in accordance with the present invention, with 4B&C illustrating the system using a coil within a tube circuit embodiment of the present invention, in which the outer tube is an accordion-like tube (e.g., Ultra-Flex®).

DETAILED DESCRIPTION OF THE INVENTION

F3™ Circuits—Circuits with Unconventional (New Era) Conduits

Figure 1:
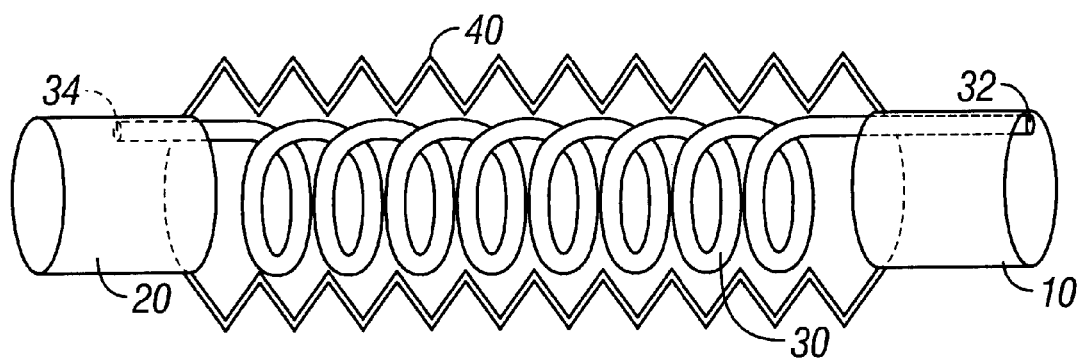
FIG. 1 is a diagram illustrating a retracted first, coiled-tube conduit contained within a compressed second conduit, with both the proximal ends of the first and second conduits being attached to a common proximal fitting, wherein a portion of the second conduit is not shown to permit viewing of the first conduit.

With reference to FIG. 1, an embodiment of the present invention is illustrated, including a multilumen breathing circuit with interacting mutually adjustable length members. This embodiment, also referred to herein as the F-Coil™ circuit, has optional proximal fitting 10 and an optional distal fitting 20. First conduit 30 is a coiled resilient tube having a proximal end 32 and a distal end 34. Proximal end 32 of first conduit 30 is connected to proximal fitting 10 and distal end 34 of first conduit 30 is connected to distal fitting 20. In an alternative embodiment, proximal fitting 10 may provide a proximal connector for tube 30. End 32 and fitting 10 may vary in diameter, shape and spatial relationship to provide for connection to any standard "F2™ type" proximal terminal, such as that described in U.S. Pat. No. 5,778,872, to Fukunaga.

In a preferred embodiment, the second or outer tube 40 is flexible and corrugated, and formed of a transparent (or semi-transparent) material. Preferred corrugated tubing includes, for example ULTRA-FLEX®, which upon axial extension from its compressed axial conformation, or vice versa, will retain its axial length (e.g., will not rebound; i.e., accordion-like pleated tubing). Further, the ULTRA-FLEX®, when bent, will retain the angle of curvature to which it is bent without substantial reduction in the tube's inner diameter. Suitable corrugated tubing for use in the present invention is used in the Ultra-Flex circuit, ULTRA-FLEX® tubing from King Systems Corporation, of Noblesville, Ind., U.S.A., or the tubing used in the Isoflex™ circuit sold by Baxter Corporation of Round Lake, Ill., USA. The tubing may be formed with integral distal and/or proximal fittings, wherein the fittings have relatively thicker or more rigid walls than the tubing, or the tubing can be bonded or welded to appropriately shaped fittings as desired.

As should be abundantly clear to one of skill in the art from the forgoing summary and definitions, there are many embodiments of the present invention that are envisioned and encompassed. For example, diameters of first and second conduits (30, 40) may vary depending on use. Also, outer tube 40 or inner tube 30 may be replaced with a suave tube. It should be clear that a coiled flexible tube may change its overall axial configuration without altering the cross-sectional shape of the lumen or lumens within it.

The outer tube 40 ends in an optional distal outer fitting 20, which is designed for ready connection to patient devices, such as an endotracheal tube, laryngeal tube, laryngeal mask or anesthesia mask.

In an embodiment, the distal end 34 of the first tube may be directly bonded to the interior of second tube 40. Optionally, the first tube may be directly bonded to the interior of second tube 40 at a series of designated points along the length of tube 40. First tube 30 may also be wrapped around the exterior of tube 40, and periodically bonded to the exterior thereof.

With reference to optional distal fitting 20, the distal end 34 of first tube 30 is shown bonded thereto. In an embodiment, distal fitting 20 is connected to an optional inner distal fitting to which the distal end 34 of first tube 30 may be connected. The length of fitting 20 may be extended and the connection point between fitting 20 and the optional distal inner fitting made axially adjustable, wherein a predetermined dead space may be provided.

Figure 2:
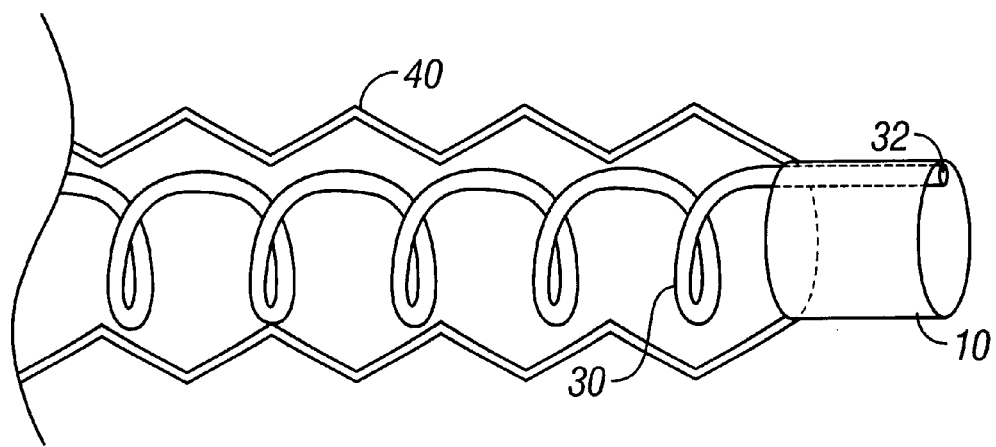
FIG. 2 is a diagram illustrating a portion of the device of FIG. 1 upon extension.
Figure 3:
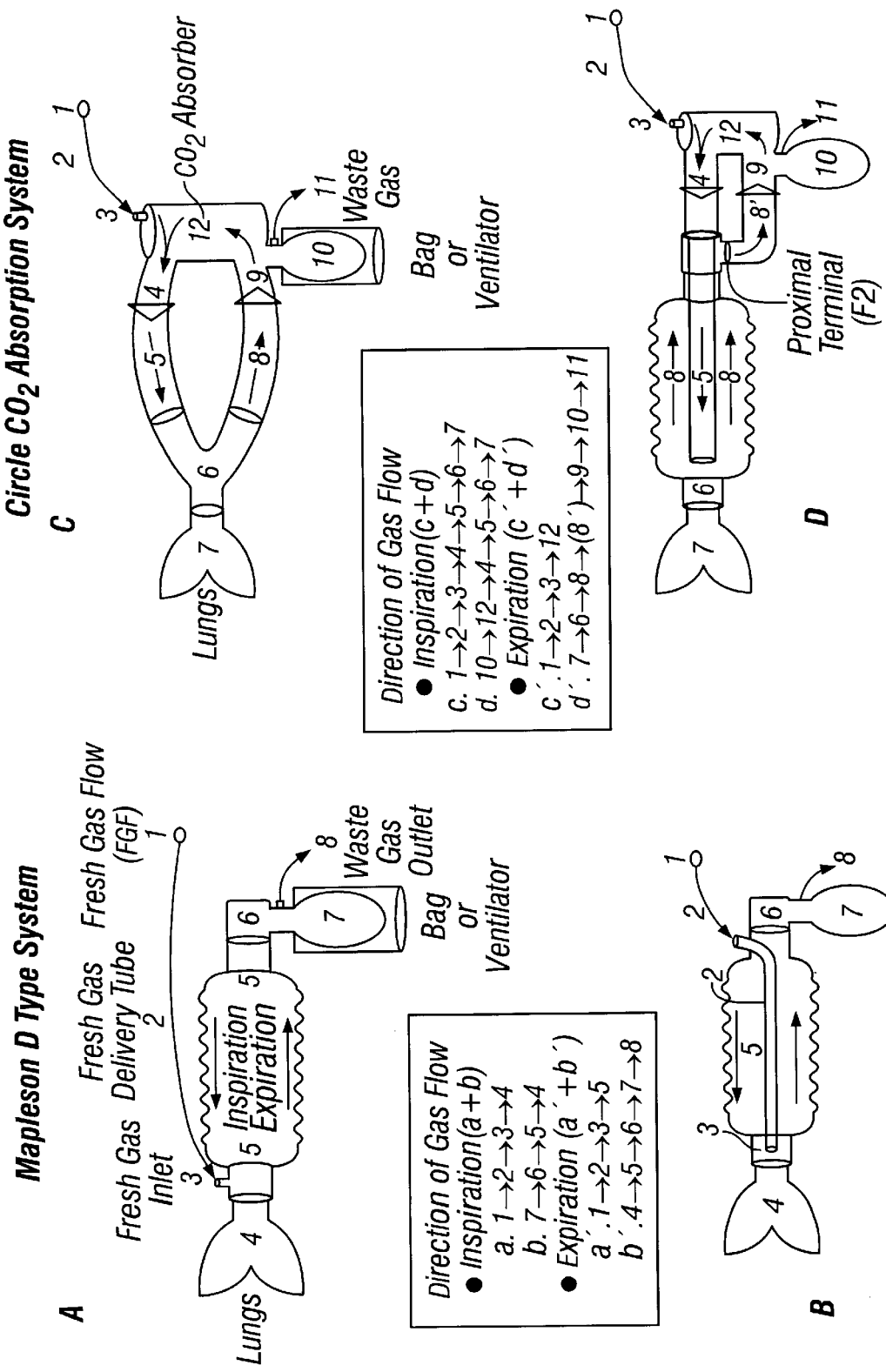
FIGS. 3A–D illustrate the operation of a Mapleson D type system and Circle $CO_2$ Absorption System.

With reference to FIG. 2, it can be seen that second conduit 40 has been axially extended, which causes first conduit 30 to axially extend. The length, diameter, number of coils per inch, and resiliency of first conduit 30 is selected to prevent kinking of first conduit 30 upon extension that would block flow therethrough, yet provide for axial retraction or rebound of coil 30 upon axial contraction of outer tube 40, without compromising the performance of the unilimb circuit. Preferably, the resiliency of the coil, or tendency to recoil, should not cause disconnection of the proximal end 32 of the inner conduit 30 from proximal fitting 10 when the outer conduit 40 is axially extended to its maximum length, and likewise it should not cause the distal end 34 of inner conduit 30 to axially move with respect to the distal end of tube 40. Inner conduit 30 can be manufactured from medical grade plastic, for example, that used to provide for respiratory gas sampling, or such as that used in intravenous fluid devices.

An axially extensible and collapsible or compressible tube (e.g., accordion-like tubing, coiled tubing, etc.) used as the first tube (which may be an inner or outer tube), and wherein the second, or inner tube or adjacent tube also expands or compresses in a synchronized manner with the first tube is greatly desirable because it promotes safety, as disconnections, obstructions and kinking are diminished. This also enhances rebreathing control and provides greater flexibility and cost effectiveness as manufacturing, storage and shipping become less expensive.

Double Coil Circuit Embodiment

Figure 5A:
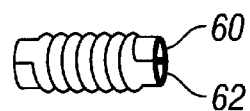
FIGS. 5A–D illustrate the components and operation of systems constructed in accordance with the present invention using the double coiled circuit embodiment of the present invention.
Figure 5B:
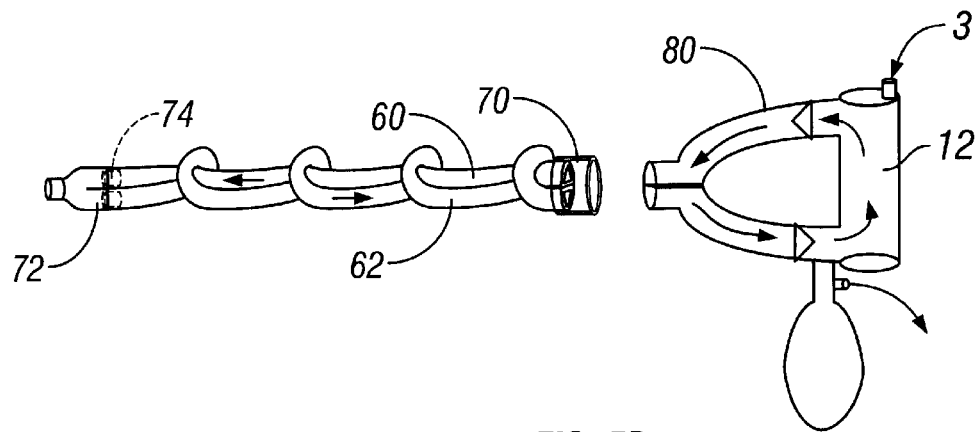
Figure 5C:
Figure 5D:
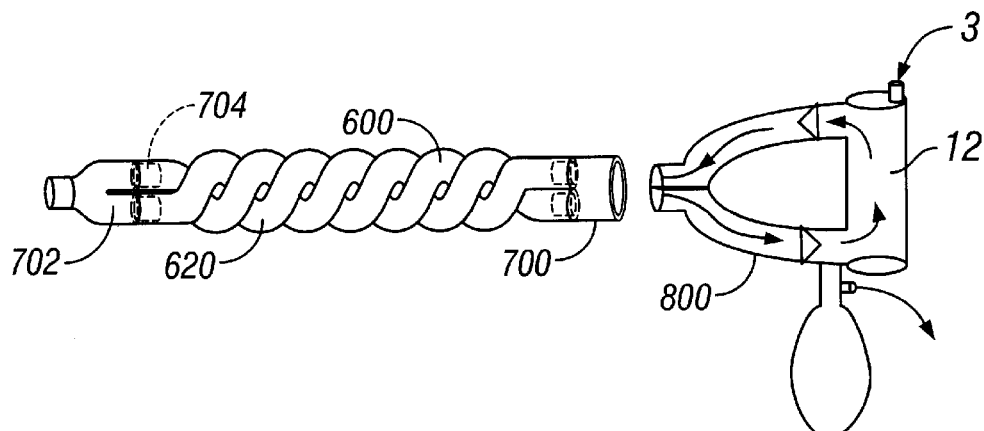

With reference to FIGS. 5A–B, an embodiment of a new circuit is illustrated. Two coiled tubes 60 and 62 are in parallel-coiled relationship to form a double coil circuit. The tubes may be bonded together at one or more external points, one tube may be formed within the other, or one tube may be divided by a common wall forming two lumens. With reference to 5B, the interaction of the members upon expansion is illustrated in an exploded view, along with their alignment with a proximal fitting 70 and proximal terminal 80 used in a circle system. Flow arrows demonstrate the paths of inspiratory gases from the FGF (fresh gas flow) inlet and to the expiratory gas outlet. Tubes 60 and 62 are connected at their distal ends to a distal fitting 72 via nipples 74. FIGS. 5C–D illustrate an alternative embodiment of the double coil illustrated in FIGS. 5A–B. Coiled tubes 600 and 620 are connected to a proximal fitting 700, which connects the respective tubes to proximal terminal 800 used in a circle system. Note that tubes 600 and 620 are interlocked by the interaction of their coils, and may optionally be periodically bonded together. As the proximal and distal openings in tubes 600 and 620 are independent, fittings can be attached on either the inside or outside of the walls of tubes 600 and 620. Tubes 600 and 620 are connected at their distal ends to a distal fitting 702 via nipples 704.

Sliding Inner Tube Circuit Embodiment

Figure 6A:
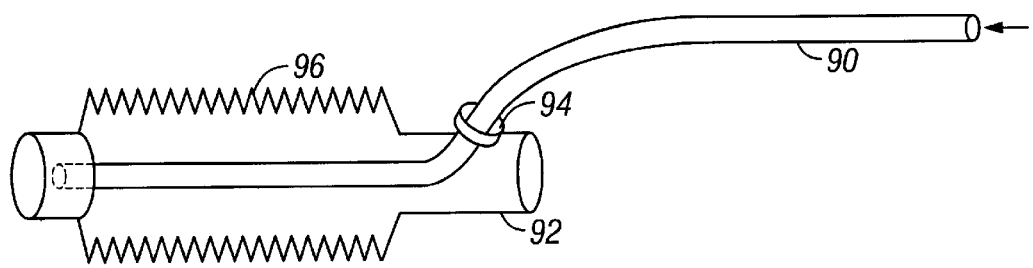
FIGS. 6A–B illustrate the components and operation of the sliding inner tube embodiment of the present invention, in which a smooth-walled conventional inspiratory gas line is inserted through a fitting into an axially expandable and collapsible tube.
Figure 6B:
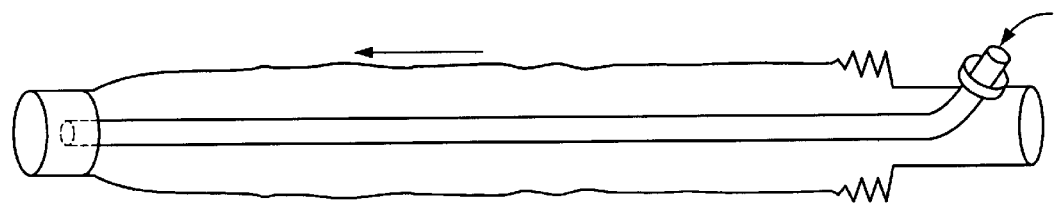

With reference to FIGS. 6A–B, the components and operation of an embodiment of a circuit in accordance with the present invention is illustrated. A first tube 90 is slidably inserted into proximal fitting 92 via sealing fitting 94. A second tube 96 is connected at its proximal end to proximal fitting 92, with a portion of tube 96 removed to reveal the first tube 90 inside. Tube 96 is axially compressible and extendable, and may be for example made of ULTRA-FLEX® tubing. First tube 90 is provided with a smooth walled portion to permit sliding in and out of fitting 92 in response to axial contraction and extension of tube 96. The mutually axial interaction of the circuit members may be accomplished by direct connection of the distal end of tube 90 to the distal end of tube 96, via a common distal fitting, or other operative connection techniques and devices.

Dual Accordion Circuit Embodiment

Figure 7A:
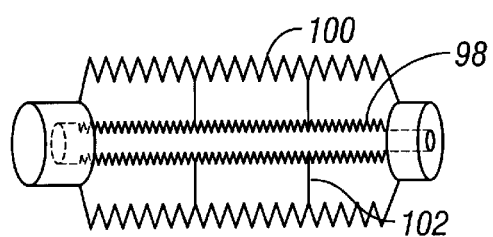
FIGS. 7A–B illustrate the components and operation of a dual coaxial accordion tube embodiment of the present invention.
Figure 7B:
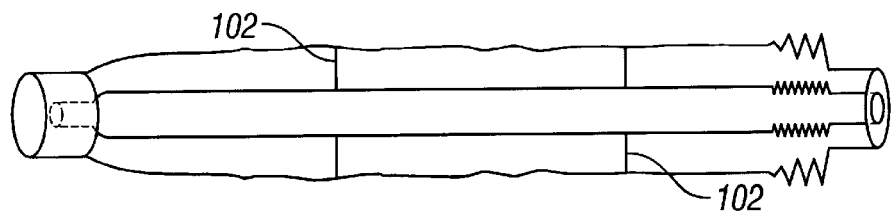

With reference to FIGS. 7A–B, the components and operation of an embodiment of a circuit in accordance with the present invention is illustrated in schematic form. Dual coaxial accordion tubes 98 and 100 may be connected at their proximal ends to each other or to a proximal fitting. The tubes 98 and 100 may both be ULTRA-FLEX® tubing. Spacing flanges or perforated disks 102 may be placed between the inner and outer tubes to optimize flow. The mutually axial interaction of the circuit members may be accomplished by direct connection of the distal ends of the tubes to each other, via a common distal fitting, or other operative connection techniques and devices, for example by a spacing flange or disk 102 placed near or at the distal end of tube 98.

Wavy Tube Circuit Embodiment

Figure 8A:
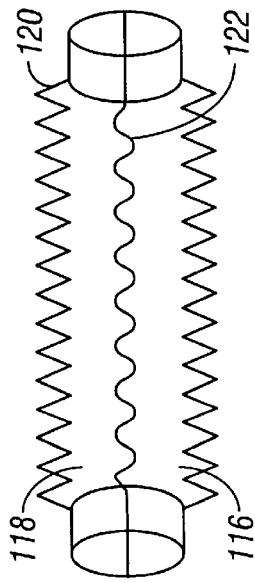
FIGS. 8A–B illustrate the components and operation of a wavy tube or sheath in an accordion tube embodiment of the present invention, with a portion of the outer tube removed to reveal the inner tube.
Figure 8B:
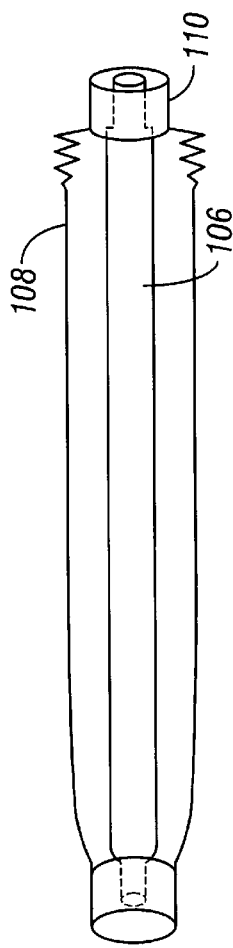

FIGS. 8A–B illustrate the components and operation of a wavy tube sheath in an accordion tube circuit embodiment of the present invention in schematic form. A relatively smooth walled tube 106 has a fixed bias to have a wavy contracted shape. Tube 106, of resilient material, can straighten when extended and return to its pre-biased contracted shape. An outer tube 108 can be extended and contracted simultaneously with tube 106. Spacing flanges or perforated disks may be placed between the inner and outer tubes to optimize flow. As with other circuit embodiments, the mutually axial interaction of the circuit members may be accomplished by direct connection of the distal end of the tubes to each other, via a common distal fitting, or other operative connection techniques and devices. Further, a variety of material can be used. For example, while tube 108 may be ULTRA-FLEX®, tube 106 may be a fabric or plastic sheath that can be elastic and radially flexible. Preferably, the axial resiliency (i.e., tendency to recoil or contract) of the inner conduits in the circuits of the present invention is insufficient to dislodge the proximal end thereof from an inspiratory gas inlet when the circuit is fully extended. For example, in drawing 8B, the tendency of tube 106 to rebound to its compressed or relaxed state, illustrated in drawing 8A, should not be sufficient to dislodge the proximal end of tube 106 from proximal fitting 110 when the fitting is held stationary and the conduits 108 and 106 extended. As noted above, tube 106 may be a fabric or plastic sheath that can be radially flexible. Thus, tube 106 may be a suave tube, and/or tube 108 may be a suave tube. For example, the inner or outer tubes of a respiratory conduit in accordance with this embodiment of the present invention may relax or collapse when not in use and expand to required patency on demand. Additional lumens can be added in this and other embodiments.

Hybrid Circuit Embodiment

Figure 9A:
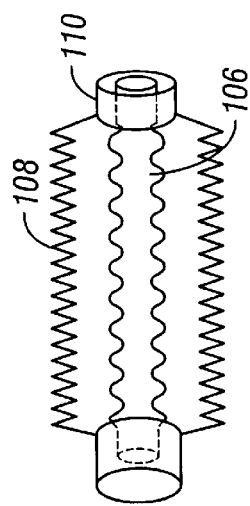
FIGS. 9A–B illustrate the components and operation of a common contractile wall embodiment of the present invention, with a portion of the outer tube removed to reveal the inner tube.
Figure 9B:
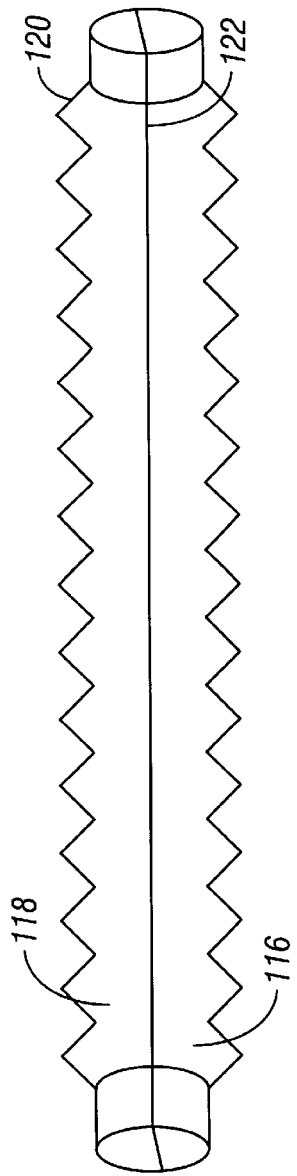

A hybrid circuit comprises conventional conduit and at least one flexible plastic sheet (e.g., polyvinyl) that forms a wall defining two or more lumens in the conduit. FIGS. 9A–B illustrate the components and operation of hybrid circuit with a common contractile wall of the present invention in schematic form. First and second tubes 116 and 118 share a common outer wall 120 that is axially expandable and contractible, and a common dividing wall 122 that can axially expand and contract with the outer wall. This embodiment may be constructed of pleated material such as that used to form ULTRA-FLEX®. Alternatively, common dividing wall 122 may be formed of a flexible plastic sheet, which permits the cross-sectional size of the two lumens to accommodate usage conditions. For example, when pressure is higher in one lumen than the other, the wall expands into the lower-pressure lumen to make it smaller than the higher-pressure lumen, while the former lumen becomes larger. Preferably, the wall has a maximum radius under respiratory care operating conditions. Additional lumens can be included, which either share the common flexible wall, or have diameters that are independent of the diameters of the other lumens. This embodiment can be formed by cutting conventional tubing in half, and bonding a flexible plastic sheet in between the two halves, or by extruding elongated hemi-circular shaped portions of plastic, and bonding a flexible plastic sheet between matching tube halves.

Relaxed Circuit Embodiments

Figure 10:
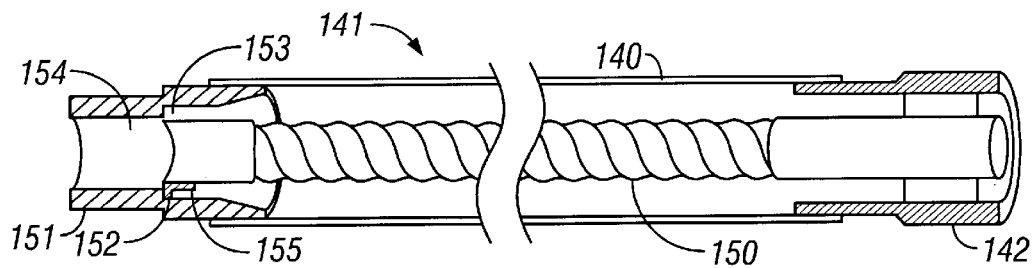
FIG. 10 illustrates the components and operation of another version of the embodiment of FIG. 8, in which a first conduit formed of a smooth plastic lamina, a suave tube, envelopes an inner tube or second conduit comprised of a corrugated tube in which the outer tube is cut away to reveal the inner tube, and an intermediate section removed to accommodate scaling of the figure. While the outer or first conduit can collapse when not being used, the inner conduit maintains its diameter during respiratory care operating conditions and during ambient and non-use conditions.

FIG. 10 illustrates the components and operation of another version of the embodiment of FIG. 8 in schematic form, in which a second conduit formed of a smooth plastic lamina, e.g., a Suave™ tube, 140 envelopes an inner tube or first conduit 150 comprised of a corrugated tube. While the outer or second conduit 140 can collapse when not being used, the inner conduit 150 maintains its diameter during respiratory care operating conditions and during ambient and non-use conditions. This embodiment makes more explicit what is stated in regards to FIG. 8, in that one of the tubes can be radially flexible. In a preferred embodiment, the respiratory conduit 141 includes a proximal fitting 142 that is bonded to proximal ends of tubes 140 and 150. The proximal fitting facilitates connection to a corresponding proximal terminal. A distal fitting 151 is connected to the distal ends of tubes 140 and 150. The distal end of tube 150 is bonded to flanges 152. Radial flanges 152 are not solid annular rings, but have gaps 153 to permit flow of gases from common zone 154 into tube 140. While tube 140 may collapse under ambient, non-use conditions, in use, tube 140 may be expanded to its maximum radius and volume during expiration as well as during inspiration (depending on whether it is used for inspiration or expiration) provided there is a sufficient flow rate of gases; there is no or minimal compliance at maximum radius. Axial flanges 155 connect to radial flanges 152 and grip the distal end of inner tube 150. Tube 150 may be bonded to radial flanges. Axial extension of radial flanges 152 and/or axial flanges 155 can provide a greater fixed dead space. As noted in other embodiments, the distal fitting, such as distal fitting 151, can be modified to provide for a sliding connection between the distal fitting main housing and the connector to the inner conduit, wherein the dead space may be adjusted to a desired volume.

Figure 11:
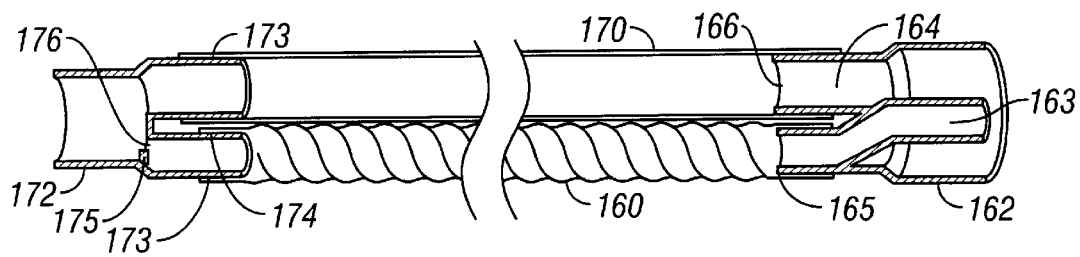
FIG. 11 illustrates the components and operation of a unilimb respiratory conduit, in which a first flexible tube is a conventional flexible corrugated or pleated tube that maintains a fixed diameter at ambient conditions and over respiratory therapy operating conditions, while the second tube is a non-conventional plastic tube that may radially collapse when patency is not required.

FIG. 11 illustrates the components and operation of a unilimb respiratory conduit in schematic form, in which a first flexible tube 160 is a conventional flexible tube that maintains a fixed diameter at ambient conditions and over respiratory therapy operating conditions, while the second tube 170 is a non-conventional plastic tube that may radially collapse when patency is not required. In a preferred embodiment, tube 170 is a suave flexible tube. A new proximal fitting 162 is illustrated, in which a coaxial flow is diverted into two independent lumens 163 and 164 that have two independent non-interfering ports 165 and 166, i.e., independent, non-interfering ports are ports that can be individually accessed without blocking or interfering with access to another port or requiring the disconnection of one port. Distal fitting 172 has axial walls 173 and 174 to which the distal ends of tubes 160 and 170 may be bonded. Extension of axial walls 173 and 174 permits for dead space adjustment. Connecting flange 175 has a gap 176 to provide for patency, while holding wall 174 in spaced relationship with wall 173.

Figure 12:
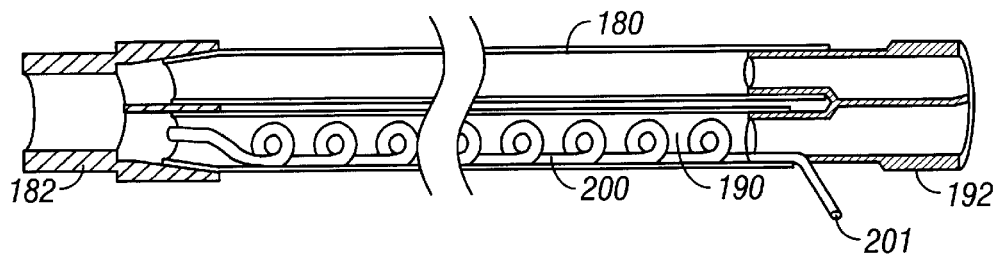
FIG. 12 illustrates the components and operation of a unilimb respiratory conduit formed of two non-conventional tubes or conduits, e.g., suave tubes, joined at their distal and proximal ends. One of the tubes includes a coiled tube, which is more radially rigid than the tube in which it is contained so as to assist in maintaining patency of its host tube.

FIG. 12 illustrates the components and operation in schematic form of a unilimb respiratory conduit formed of two non-conventional tubes or conduits 180 and 190, e.g., suave tubes, joined at their distal ends by distal fitting 182 and at their proximal ends by proximal fitting 192. Tube 190 includes a coiled tube 200, which is more radially rigid than the tube in which it is contained so as to assist in maintaining patency of its host tube. Tube 200 may be used for gas sampling or other purposes. For example, tube 190 may provide inspiratory gases. Tube 190 is held patent by the coiled tube 200, and tubes 180 and 190 are of fixed axial length. The recoiling of tube 200 causes tubes 180 and 190 to collapse axially. In an embodiment, tube 200 includes a wire of metal or plastic that maintains whatever length it is extended to rather than being axially elastic as in other embodiments. The inner wall of tube 190 is optionally bonded at periodic intervals to tube 200 so as to provide for even folding and extension of the fabric forming tube 190. In an embodiment, tube 200 is a solid wire.

Fitting 192 provides for rapid connection of the respiratory conduit to a corresponding multilumen proximal terminal. While outlet 201 of tube 200 is shown passing through the wall of fitting 192, fitting 192 may have an extra lumen for connecting tube 200 to a corresponding inlet or outlet.

The above non-limiting examples describe breathing circuits, also referred to as multilumen unilimb respiratory conduits, which axially and/or radially expand or contract. However, the breathing circuit does not need to expand or contract axially. An embodiment may comprise one fixed length conduit that is a conventional corrugated tube or a smooth resilient tube having a pipe-like configuration or an ULTRA-FLEX® tube, and the second conduit can be a non-conventional conduit. Hence, the respiratory conduit can be of fixed length, and one or more of the tubes in it may radially expand and contract.

A breathing circuit or unilimb respiratory conduit of the present invention can be readily connected to a respirator or ventilator, or to an anesthesia machine either via the proximal fitting of the respiratory conduits or via a proximal terminal, such as the one described in U.S. Pat. No. 6,003,511. By matching the proximal end of the proximal fitting to a unilimb respiratory conduit of the present invention to a corresponding proximal terminal, respiratory conduits in accordance with the present invention can be provided for quick and safe connection to a variety of respiratory devices, including but not limited to anesthesia machines and ventilator machines. This can be done directly or via a filter. A breathing circuit of the present invention can be connected to a single filter or a multilumen filter, or manufactured integrally with a monolumen or multilumen filter. The proximal end of the filter housing can be configured for quick and safe connection to a proximal terminal of a machine, and the distal end of the filter housing can match the configuration of the proximal end of the respiratory conduit.

Respiratory conduits of the present invention can also be used to ventilate patients during transport, or be connected to a gas source (e.g., oxygen source in the post-anesthesia care setting, emergency room, etc.). Thus, the breathing circuit of the present invention is a multi-purpose breathing circuit. Instead of utilizing a new device, such as an expensive ambubag for transport, the same breathing circuit of the present invention can be utilized to provide oxygenation during transportation of a patient, for example to the PACU or other location. After the patient is transported for example from the operating room to the PACU, the same breathing circuit can be utilized to oxygenate the patient in the PACU, without the need to utilize an additional oxygen supply device, such as a nasal cannula or clear oxygen mask provided with an oxygen tube or a T piece set.

Operation of Mapleson D Systems and Circle $CO_2$ Absorption Systems

With reference to FIGS. 3A–D, drawing 3A illustrates a schematic diagram of a Mapleson D system, in which the fresh gas flow ("FGF") 1 is provided via fresh gas delivery tube 2 (shown in schematic form only) to a distal fitting 3. The operation of the system is better understood by reference to the numbered arrows and or part numbers. For example, during inspiration, gas to lungs 4 flows simultaneously from fresh gas flow inlet 1 and bag 7 via flow paths a and b described in the key below FIG. 3A and by reference to part numbers and numbered arrows as follows: (1→2→3→4)+(7→6→5→4). During expiration, gases flow from lungs 4 to waste gas outlet 8 via flow paths a' and b' as follows: 4→5→6→7→8.

Drawing 3B illustrates a Bain circuit used with a Mapleson D system. A key feature of the Bain is that the fresh gas tube 2 is inserted in the proximal terminal at the proximal end of the circuit and the tube extended through breathing tube 5 to have its distal end 3 at the distal end of the circuit.

Drawing 3C illustrates a circle $CO_2$ absorption system, which has a $CO_2$ absorber 12, check valves (i.e., unidirectional valves) 4 and 9, as well as inspiratory conduit 5 and expiratory conduit 8 that meet at distal fitting 6. During inspiration, gas to lungs 7 flows simultaneously from fresh gas flow source 1 and bag 10 via flow paths c and d in the key below FIG. 3C as follows: (1→2→3→4→5→6→7)+(10→12→4→5→6→7). During expiration, gases flow from lungs 7 to waste gas outlet 11 via flow paths c' and d' as follows: (1→2→3→12) +(7→6→8→9→10→11.

Drawing 3D illustrates a circle $CO_2$ absorption system, which uses either a Universal F® or Universal F2® circuit using an F2™-type proximal terminal. Inspiratory conduit 5 is coaxial within expiratory conduit 8 distal of the proximal terminal.

It is important to note that in the circle system, fresh gases are combined with recirculated scrubbed gases near or at the $CO_2$ absorber, and carried in a common conduit 5 to the patient. In contrast, the Mapleson D system provides the fresh gases at the distal end of the circuit.

Gas Conservation System: "F3™ Combo System"

Figure 4A:
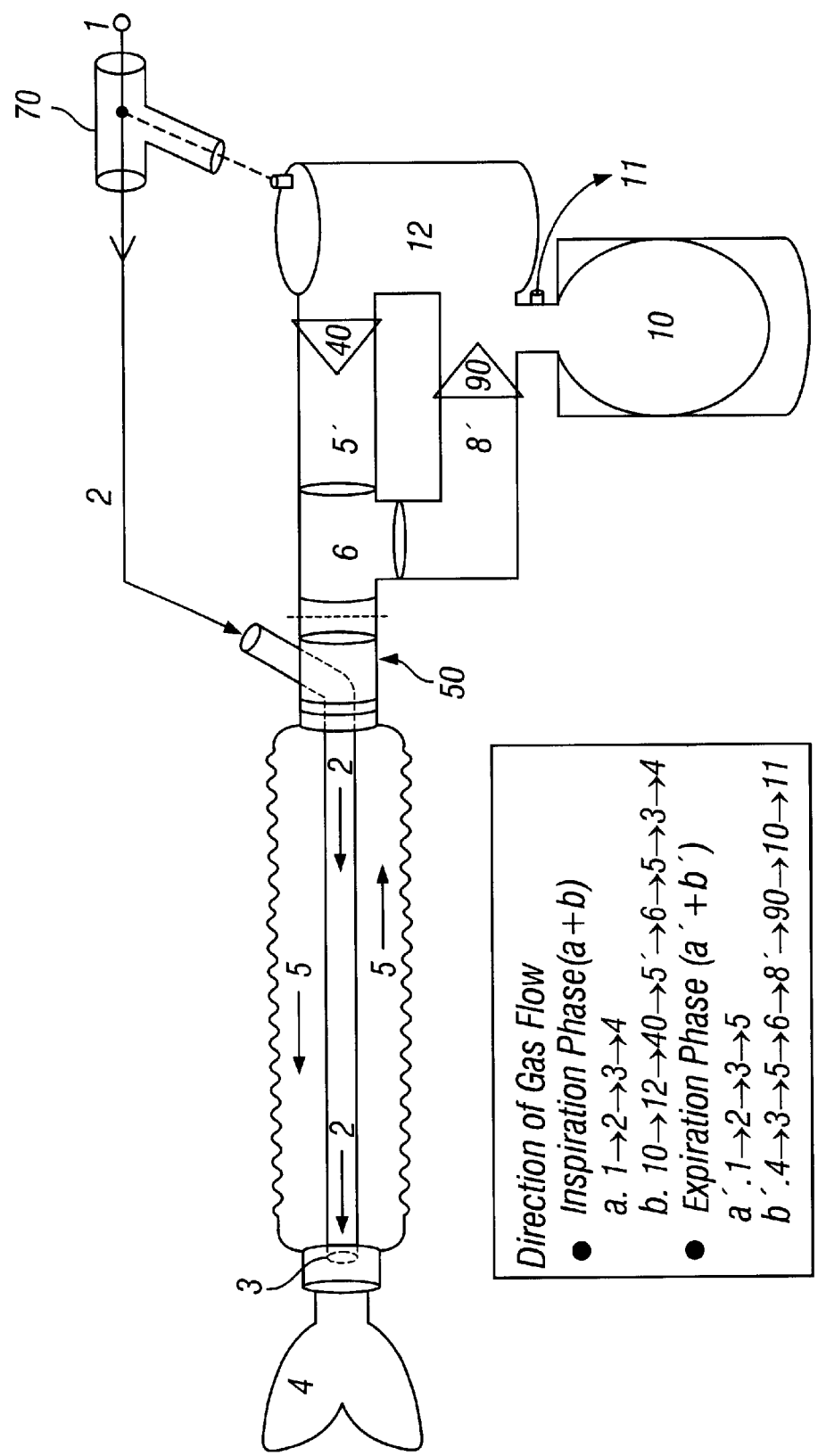

With reference to FIG. 4, drawing 4A illustrates an assisted ventilation system of the present invention utilizing an embodiment of a new breathing circuit of the present invention. Fresh gas flow from a source 1 (e.g., an anesthesia machine) passes via flow diverter 70 through fresh gas delivery tube 2 (shown in schematic form only). Flow diverter 70 is optional as it is provided for modifying a circle system having a fresh gas input port in the scrubber circuit (generally near or at the $CO_2$ absorber). The flow diverter closes off the fresh gas input port on top of $CO_2$ absorber 12 so that fresh gases can be directly fed to the distal end 3 of the breathing conduit (i.e. FGF bypasses the scrubber module so it is not mixed with scrubbed gases). A seal could be used in place of the flow diverter, and the fresh gas source could come from a variety of locations. In this embodiment, tube 2 is, as with a Bain, rigidly bonded to proximal fitting 50, and fresh gases are delivered directly to the distal end 3 of the breathing circuit, which continuously feed the common inspiratory/expiratory conduit 5, also referred to as a rebreathing tube. However, with reference to drawing 4C, unlike a Bain, the dimensions of conduit 5 can be altered so that the tube volume and the concentration of its contents are altered so that the inspired concentration of gases can be adjusted for each patient, and rebreathing can be controlled. For example, tube 5 may be an ULTRA-FLEX® tube. Control can be achieved by adjusting the dimensions of tube 5, for example by axially adjusting the length of tube 5 (titration of tube volumes and contents in response to inspired and/or end-tidal gas concentration data provided by the monitoring equipment).

Note that unlike the conventional circle system, in the new system of the present invention the fresh gases delivered directly from the anesthesia machine are not mixed or diluted at the machine/scrubber circuit end. Because the fresh gas flow is delivered close to the patient, the inspired anesthetic concentrations are almost equal to the delivered concentrations. Thus, the anesthetist can rely on the anesthetic concentrations reported by the flow meter and the vaporizer as indicative of the inspired concentrations. In contrast to the Mapleson D system, in the new system the expired gases are not all disposed of but are reused as "refreshed gas," as expired gases pass through a scrubber module for recirculation. This new "F system" provides a surprising improvement in the control and quality of respiratory and anesthetic ventilation while avoiding waste of anesthetic gases. If a coiled fresh gas tube is used, upon contraction of tube 5, tube 2 coils to contract, as can be seen in FIG. 4C. The fresh gas tube 2 can have other shapes and can be arranged to be an inner or outer tube with respect to tube 5. If tube 2 is smooth-walled, it can slide in and out of a fitting as shown in FIG. 6. Preferably, the volume of tube 5 during use is adjusted to be larger than the tidal volume ($V_T$) to minimize mixing of the fresh gases with the "scrubbed gases". This allows optimal utilization of the fresh gases (anesthetic agents) as well as O2 and CO2 rebreathing control.

In a preferred embodiment, the length of the rebreathing tube may be variable for multiple usages. The same breathing system may be universally used, in an operating room, ICU, emergency room, respiratory care ward, in adult and pediatric cases, etc.

Drawing 4B illustrates a proximal terminal 52 in schematic form that may be separately detached and connected to breathing conduit 5 and fresh gas tube 2. An additional proximal terminal 6 is also shown in schematic form. Terminal 6 can be an F2® type or Y adaptor. Referring back to drawing 4A, the system components also preferably includes a reservoir bag or ventilator device 10, waste gas outlet 11, which may be attached to a scavenger, $CO_2$ absorber 12, check valves 40 and 90, inspiratory conduit 5', expiratory conduit 8', and a proximal terminal 6 that connects to proximal fitting 50.

The operation of the system is better understood by reference to the numbered arrows and or part numbers. For example, in a preferred embodiment, during inspiration, gas to lungs 4 flows simultaneously from fresh gas flow source 1 and bag/ventilator 10 as follows: (1→2→3→4)+(10→12→40→5'→6→5→3→4). During expiration, gases flow from lungs 4 to waste gas outlet 11 as follows: (1→2→3→5)+(4→3→5→6→8'→90→10→11).

Thus, in a preferred embodiment, a new ventilation and anesthesia system is provided, comprising a recirculation module, a rebreathing tube operatively connected at its proximal end opening to the recirculation module for providing expired gases to and receiving gases from the recirculation module, and a distal input for fresh gases, wherein the distal input is located in the distal portion of the rebreathing tube or in a distal fitting operatively connected to the distal end of the rebreathing tube. The recirculation module preferably includes a scrubbing circuit, which may include at least two unidirectional valves, an expiratory input conduit, CO2 absorber, exhaust vent, scrubbed gas output conduit, and squeeze bag and/or ventilator. In a preferred embodiment, a filter device can be detachably connected at the proximal end of the rebreathing conduit 5; the filter device may also be integrally formed with conduit 5. A preferred embodiment of this new system is referred to as an F3™ COMBO system.

A System that Optimizes Utilization of Fresh Gases that is Also More Efficient and Safer It is well recognized that methods of low flow anesthesia have considerable advantages over high flow anesthesia methods because they reduce the amount of wasted anesthetic gases, therefore, they are more economic and reduce healthcare costs. Moreover, such methods maintain better humidification and temperature of the inhaled gases. They also minimize the amount of gas released from the system to the environment, reducing operating room pollution, which provides a safer working environment and in general less air pollution. However, despite numerous advantages of low flow anesthesia techniques, the use of these methods and associated systems is hampered by numerous limitations that make them unsafe. Therefore, there is a need to improve these systems and methods.

Traditionally, high fresh gas flow, defined as flow greater than five liters per minute (FGF>5 L/min), has been used in a conventional anesthesia circle breathing system with $CO_2$ absorption, and over 7 L/min in the Mapleson D system. However, more than 90% of the newly delivered fresh gases are wasted. One of the main reasons for high flow anesthesia practice is the fear of over-dosing or under-anesthetizing the patient when low flow anesthesia is provided. With high fresh gas flows, the inspired (anesthetic) gas concentration (FI or $F_I$) can be assumed to be equivalent to the delivered gas concentration (FD or $F_D$=vaporizer setting concentration). Such an assumption cannot be made with low flow anesthesia. Lowering the FGF results in a gradually increasing gradient (difference) between the delivered gas concentration (FD) and the patient's inspired gas (FI), which is in part due to the increasing dilution of the fresh gas with the scrubbed gases within the system. For example, during low FGF of less than 3 L/min, there are significant discrepancies (over 20%) between the inspired gas concentration and the delivered gas concentration. This may result in under-anesthetized patients. Therefore, low flow anesthesia has not been recommended unless continuous flow adjustments are made during anesthesia and by very careful monitoring the inspiratory and the end-tidal gas concentrations.

EXAMPLES

The following hypotheses were tested: a) The inspired and the delivered fresh gas concentration (FI/FD) ratio is dependent on the fresh gas flow (FGF) over time; and b) Using the F3™ COMBO system the $F_I/F_D$ ratio can be improved at low flows.

The effects of lower FGF on patients' inspired gas concentrations were compared to the delivered gas concentrations (i.e., anesthetic concentrations indicated by the vaporizer's dial setting) during general anesthesia.

After obtaining institutional approval and patient consent, a total of 34 healthy (ASA class I) adult patients undergoing elective surgery were included in the studies. The studies were conducted using standard methods of anesthesia: Anesthesia was induced with thiopental and endotracheal intubation was facilitated with 1 mg/kg succinylcholine. Anesthesia was initially maintained with high flow (5 L/min) of 3/2 $N_2O$—$O_2$ mixture and 1.5% isoflurane as per vaporizer setting using the standard anesthesia circle system with $CO_2$ absorption. The patient's lungs were mechanically ventilated using the traditional mode of intermittent positive pressure ventilation with a tidal volume of 10 ml/kg, ventilation frequency (10–12 breaths/min) and inspiratory/ expiratory ratio (1:2). The above parameters were kept constant throughout the study. Fraction of delivered ($F_D$), inspired (FI) and end-tidal (FET) anesthetic gas concentrations were continuously monitored by mass spectrometry (Medical Gas Analyzer 100; Perkin-Elmer, Pomona, Calif.).

Figure 14:
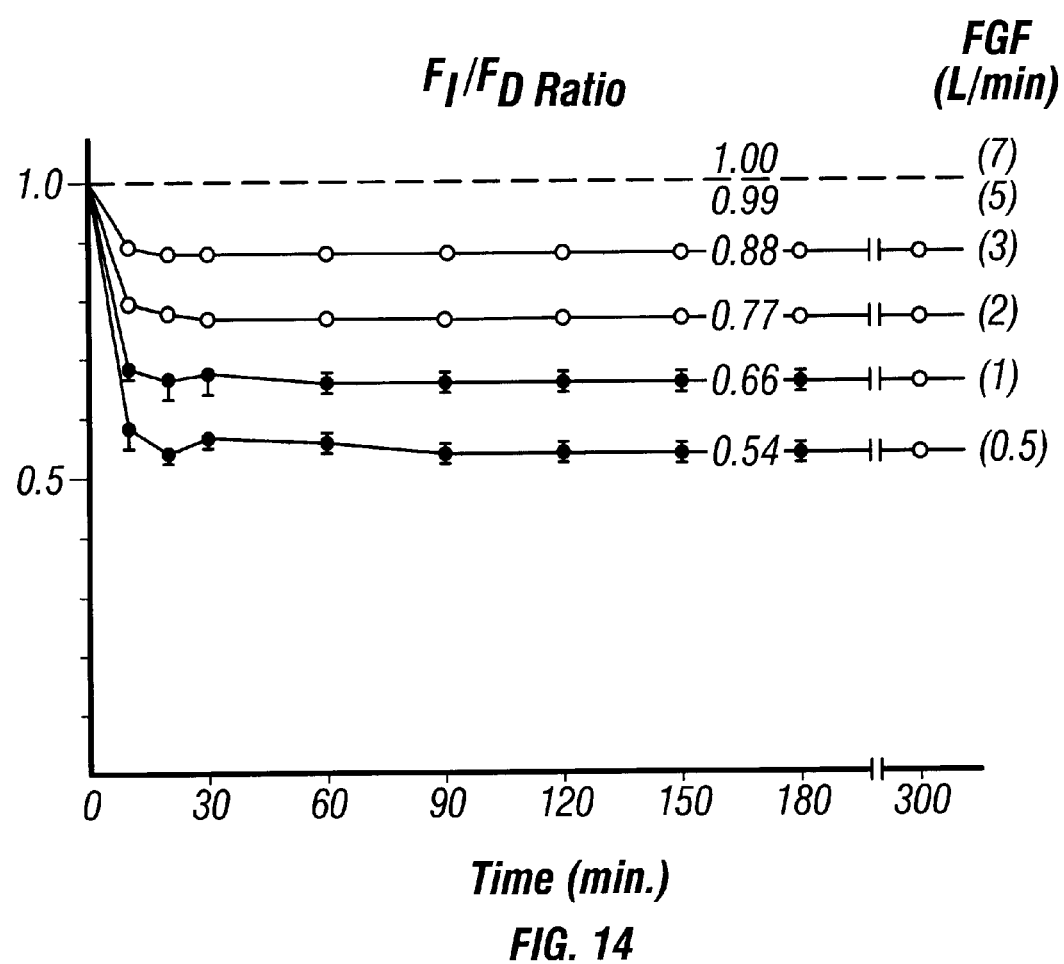
FIG. 14 is a graph illustrating the relationship of inspired ($F_I$) and delivered ($F_D$) isoflurane concentration during graded low fresh gas flow (FGF) anesthesia.

In study I, after 15 min of stabilization with high fresh gas flow (FGF>5 L/min), FGF was changed to lower FGF, selected from 4 L/min (n=3), 3 L/min (n=3), 2 L/min (n=3), 1 L/min (n=6) and 0.5 L/min (n=6), which was assigned randomly, while the same vaporizer setting (1.5% isoflurane) was maintained. Measurements of $F_I$ and $F_{ET}$ and $F_D$ were repeated for comparison of $F_I/F_D$ ratios and statistical analysis. The results of the study are summarized in FIG. 14. The results demonstrate that as the FGF is lowered the $F_I/F_D$ (or FI/FD) ratio is significantly decreased in a parallel way. Furthermore, the study shows that there is indeed a significant discrepancy between $F_I$ and $F_D$ and points out the limitations of low flow anesthesia when the conventional circle system is utilized.

Table 1 shows data from Study II, in which 12 patients were randomly assigned to group A, using the conventional circle system (n=6), and to group B, using the F3™ COMBO system during a low flow anesthesia (1 L/min) FGF. Notice in Table 1 that the $F_I$ concentration and the $F_I/F_D$ concentration ratios are greatly improved in group B wherein the F3™ COMBO system is utilized. It also shows that the difference between the $F_I$ and $F_D$ are minimal and that the new system provides a better correlation. This supports the hypothesis that low flow anesthesia can be safely administered by using the F3 COMBO™ system, and over-dosing or under-dosing of anesthetics can be avoided.

With the present F3 COMBO™ system, the anesthetist will be able to better control the inspired concentration of anesthetic gases in a more accurate and predictable manner. Therefore, even in the absence of expensive multi-gas monitoring equipment, a safe and reliable low flow anesthesia can be achieved. Also, recovery from anesthesia can be accelerated at the end of surgery and anesthesia. This can be accomplished by providing high flows of oxygen directly at the distal end so that the residual anesthetic in the lungs and the breathing circuit will be washed out very quickly. Quick recovery from anesthesia can save anesthesia recovery time and money. Therefore, the F3 COMBO™ circuit and/or methods for utilizing same can conserve anesthetic gases as well as oxygen, while minimizing pollution and health hazards, and thus improve breathing/anesthesia system efficiency. This will result in an overall lower health care costs, while optimizing patient health care.

Figure 15:
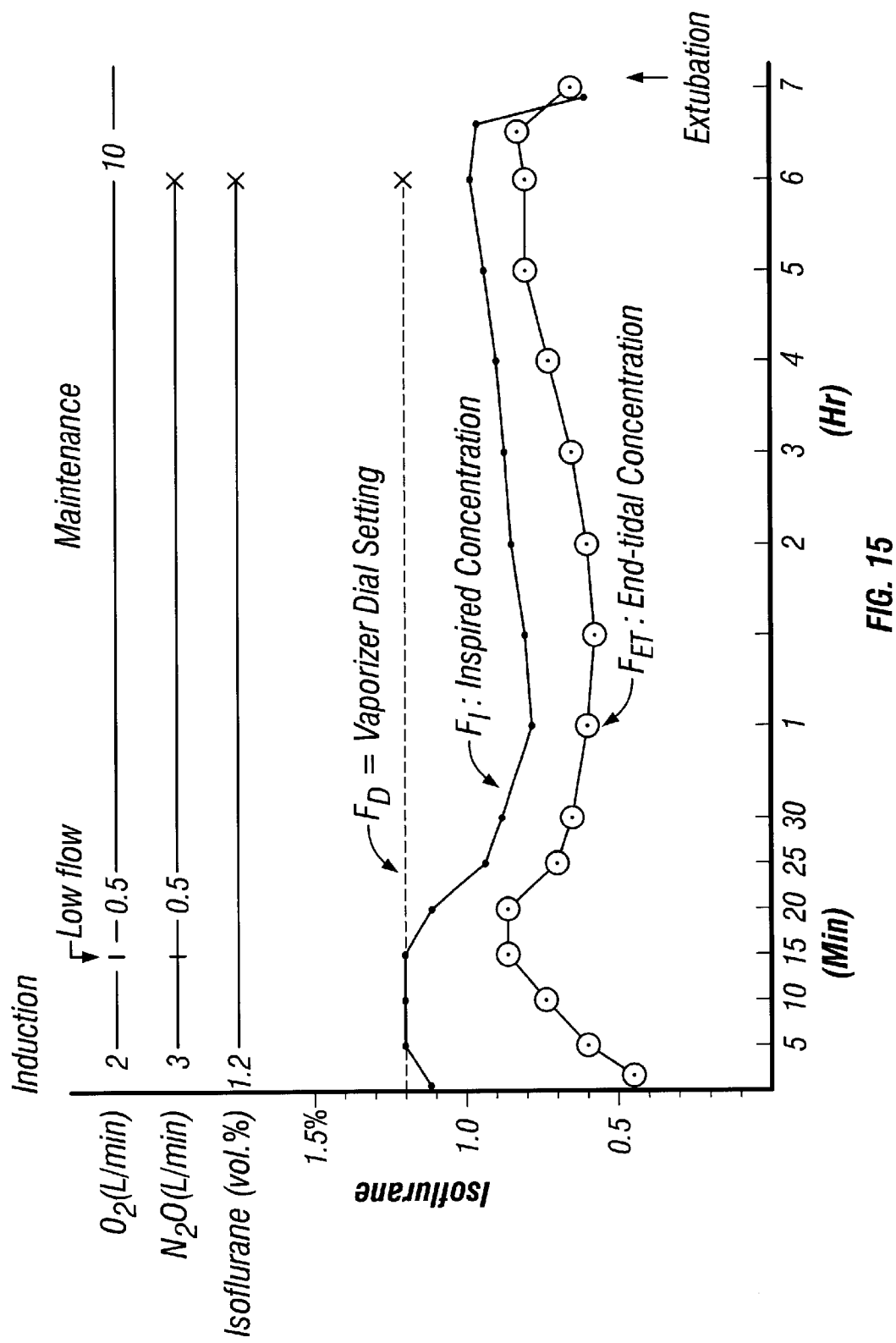
FIG. 15 is a graph illustrating the relationship of inspired ($F_I$) and end tidal ($F_{ET}$) concentration to delivered ($F_D$) concentration with a constant vaporizer setting of 1.2% isoflurane during low flow anesthesia (1 L/min FGF).

FIG. 15 shows the changes of continuous and simultaneous monitoring of the delivered ($F_D$), inspired ($F_I$) and end-tidal ($F_{ET}$) gas concentration during low flow anesthesia of 1 L/min with a constant isoflurane vaporizer setting of 1.2% over time. Notice the significant difference between the $F_D$ gas concentration (i.e., vaporizer setting concentration) and the $F_I$ and $F_{ET}$ gas concentration.

TABLE 1

Effect of diverting the FGF to the distal end of the circuit on the $F_I$ and $F_I/F_D$ ratio during low flow isoflurane anesthesia (1 L/min) using a conventional system versus the F3 COMBO ™ system

| Patient No | Vaporizer Setting ($F_D$) Vol. % | Group A (n = 6) Without Diverting FGF* (i.e., gas provided at machine side) | | Group B (n = 6) Diverting FGF** (i.e., gas provided at patient end) | |
|---|---|---|---|---|---|
| | | ($F_I$) Vol % | ($F_I/F_D$) | ($F_I$) Vol % | ($F_I/F_D$) |
| 1 | 1.5 | 0.92 | 0.61 | 1.46 | 0.97 |
| 2 | 1.5 | 0.96 | 0.64 | 1.20 | 0.80 |
| 3 | 1.5 | 1.00 | 0.67 | 1.20 | 0.80 |
| 4 | 1.5 | 1.20 | 0.80 | 1.45 | 0.97 |
| 5 | 1.5 | 0.89 | 0.59 | 1.20 | 0.80 |
| 6 | 1.5 | 0.95 | 0.63 | 1.35 | 0.90 |
| Mean ± SD | 1.5 ± 0.0 | 0.99 ± 0.11 | 0.66 ± 0.08 | 1.31 ± 0.13 | 0.87 ± 0.08 |

$F_I$: Inspired concentration;
$F_D$: Delivered concentration (as per vaporizer setting);
$F_I/F_D$: Concentration ratio.

As is now clear, the present invention provides a method of providing assisted ventilation or anesthesia wherein fresh gases are provided at low flow, for example a volume of about 1 liter per minute (flows considered low range from about 0.5 to less than 5 L/min, or less than 3 L/min in preferred embodiments), and the $F_I/F_D$ concentration ratio can be maintained at a desired level, for example above about 0.80 or higher, by adjusting the volume of the rebreathing tube proximal of the fresh gas input. In a preferred embodiment, fresh gas flows from about 1 to about 3 L/min are used, and more preferably from about 1 to about 2 L/min.

An Exemplary Dispenser

The present invention permits use of smaller respiratory conduits, and disposable components therefore. Currently, multiple circuits must be used for a single day's surgeries. This requires that the circuits be stored in or near the operating room. To prepare for each surgery, a new circuit is removed from a sterile package, and the bag is disposed of. If care is not taken in opening the bag, the circuit can be damaged.

Figure 16:
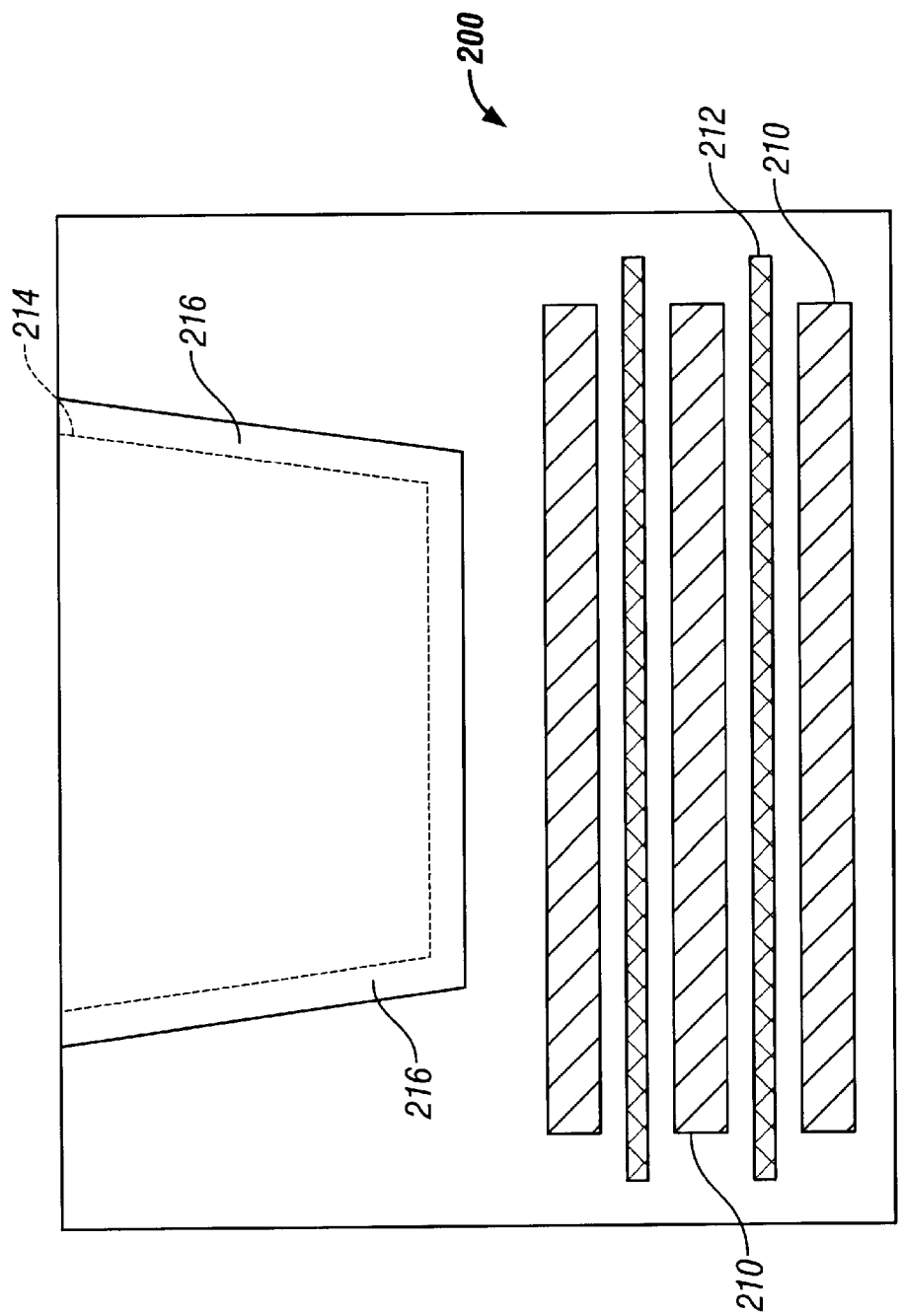
FIG. 16 illustrates an exemplary dispenser for dispensing multiple respiratory conduits, the latter being shown in block form.

Since the present invention enables less circuit components to be disposed of, the new circuit components required for each procedure are reduced. Further, due to the ability to axially contract, and in certain embodiments radially contract, the components, the respiratory conduits can be made much smaller for packaging, storage, and transport. With reference to FIG. 16, a dispenser box 200 is illustrated. Shown in block diagram are respiratory conduits 210, optionally sandwiched between thin protective plastic sheets 212. Preferably, the respiratory conduits 210 are not individually wrapped. In an embodiment, box 200 includes a line of perforations 214 on its face and top to permit tearing removal or rotating or pivoting elevation of a portion of the box. A sealing tape 216 can be provided over perforations 214 to reduce the chance of accidental opening or tampering. Boxes of varying quantities can be provided, for example, 4, 6, 8, 10, 12, 15, 24 or more than 100 respiratory conduits. The box flap may close under gravity or seal between uses. Loading of such a dispenser box eliminates the need for sealing individual disposal circuit components in separate bags, as well as reduces the time to open and remove bag contents. The dispenser box also reduces the amount of waste generated as less material is disposed of than when individual sealed bags are used.

In an embodiment, the respiratory conduits are essentially cylindrical in their cross-sectional shape. Hence the dispenser box may have a thickness and length sufficient for one respiratory conduit in its compressed form, and a height proportional to the number of conduits therein. The perforations for the box flap may extend the length of one side of the box, and box incrementally opened at the perforation to access each conduit in order.

Figure 13A:
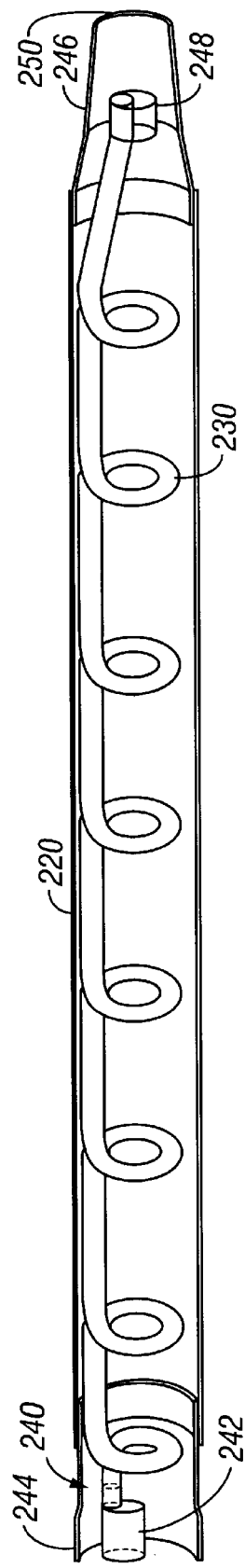
FIGS. 13(a) and (b) illustrate a respiratory conduit in expanded form (a) and compressed form (b), in which the outer or first conduit is a suave tube with a portion removed to reveal the inner tube, and the inner conduit is a coiled tube wherein the coiled tube lumen has a relatively rigid cross-sectional shape.

As can be seen by the unilimb respiratory conduit illustrated in FIGS. 13(a) and (b), multilumen conduits of the present invention come in a variety of forms, and can be compressed into relatively small volumes for shipping and storage. Hence, a plurality of such conduits can fit nicely into the dispensers described above.

Figure 13B:
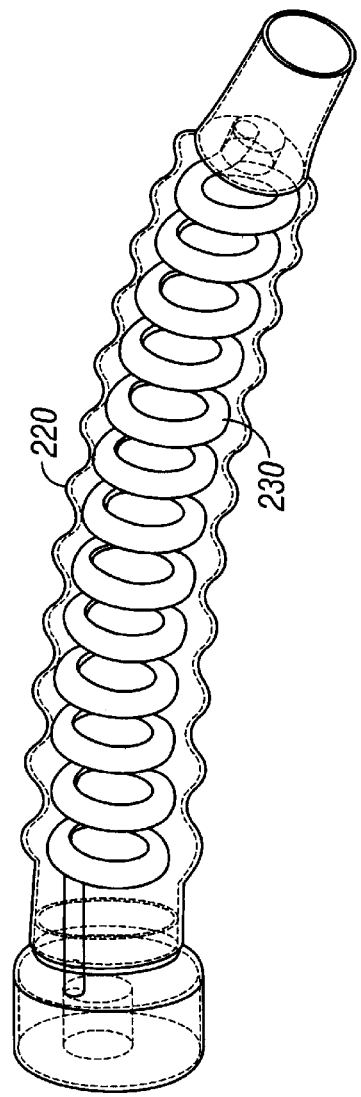

With further reference to FIG. 13, a respiratory conduit is shown in expanded form (a) and in compressed form (b). An outer or first conduit 220 is a suave tube, and the inner conduit 230 is a coiled tube wherein the coiled tube lumen has a relatively rigid cross-sectional shape. When compressed, excess fabric in suave tube 220 takes on a ruffled or wrinkled appearance. The wrinkles may be evenly distributed by periodic attachment of tube 220 to inner tube 230. Proximal fitting 240 is coaxial, with the distal end of coiled tube 230 being bonded to an inner pipe 242 or being integral therewith, although other variations are possible.

In an alternative embodiment, a rigid inner pipe and rigid outer pipe are held together by rigid spacing means to form a proximal fitting to which inner and outer conduits can be connected. Thus, the present invention allows for optimization of respiratory conduit manufacture that can depend upon the machinery, parts, materials, and skills available. Inner pipe 242 can be integrally formed with rigid coil 230 in one step. In another step, inner pipe 242, integrally formed to coil 230, can be bonded to an outer pipe, such as pipe 244, with appropriate spacing means. A suave tube can then be bonded to outer pipe 244. A single distal fitting 246, with an inner member 248 and an outer member 250 can be bonded to the corresponding tubes prior to bonding of the suave tube to the proximal fitting. The distal fitting 246 can also be constructed in a series of steps as it is connected to the tubes. For example, inner member 246 can be integrally formed to the distal end of tube 230 when the proximal end of tube 230 is bonded to inner pipe 242. Various combinations of construction steps are possible.

It should be clear to one of skill in the art that the F3™ circuits described herein are not limited to a unilimb tubing arrangements, but can also use dual limb arrangements in which at least one tube is a suave or coiled tube, which can lead to significant reduced costs in manufacturing, shipping and storage.

Thus, exemplary embodiments and uses of the present inventions have been described. Alternative embodiments, descriptions and terms are contemplated. For example, the conduits in the circuit may be of different sizes from one another, and more than two lumens may be present. Using the present invention, larger or smaller diameter conduits may be used, and both circle circuit and Mapleson type circuits may be constructed.

While exemplary embodiments of the present invention have been set forth above, it is to be understood that the pioneer inventions disclosed herein may be constructed or used otherwise than as specifically described.

What is claimed is:

1. A ventilation or anesthesia system, comprising a recirculation module, a rebreathing tube operatively connected at its proximal end opening to the recirculation module for providing expired gases to and receiving gases from the recirculation module, and a distal output for fresh gases, wherein said distal output is located in the distal portion of said rebreathing tube or in a distal fitting operatively connected to said distal end of said rebreathing tube, wherein said rebreathing tube has an adjustable volume proximal of said distal output, wherein the concentration of fresh gases administered to a patient or mammal connected to said system relative to gases that a patient may rebreath may be adjusted by adjustment of the volume of said rebreathing tube volume proximal of said distal output, wherein when the volume of said rebreathing tube is adjusted said rebreathing tube substantially retains the adjusted volume.

2. The system of claim 1, wherein said recirculation module comprises a scrubbing circuit.

3. The system of claim 1, wherein said rebreathing tube comprises accordion-like pleated tubin, and wherein said circuit is a unilimb circuit.

4. The system of claim 3, further comprising a filter.

5. A method for providing anesthetic and respiratory gases at low flows to a human or other mammal, comprising providing a patient with a fresh gas flow of desired gases and a scrubbed gas flow of recirculated gases, wherein the fresh gas flow and scrubbed gas flow are provided to the human or other mammal via a breathing circuit having a distal and proximal end and comprising a first tube and a second tube, wherein the second tube has a distal end and a proximal end, wherein the proximal end of the second tube is operatively connected to a scrubbing module for scrubbing and recirculating at least a portion of expired gases received thereby, and the first tube has an output that is operatively connected to said distal end of said circuit, wherein the first tube provides fresh gases to the human or other mammal via the distal end for the circuit said method further comprising the steps of adjusting the volume of the second tube proximal of the first tube output connection with the circuit, wherein the ratio of fresh gases to scrubbed gases administered may be adjusted by adjustment of the volume of said second tube, and said second tube retains the volume to which it is adjusted.

6. The method of claim 5, wherein fresh gases are provided at a volume of about 0.5 liter per minute to 5 L/min.

7. The method of claim 6, wherein the first and second tube comprise accordian-like pleated tubing, and wherein said circuit is a unilimb circuit.

8. The method of claim 5, wherein the ratio of inspired gas concentration to delivered gas concentration is maintained at more than about 0.80 by adjusting the volume of the second tube.

9. The method of claim 5, wherein the first and second tube comprise accordion-like pleated tubing.

* * * * *